United States Patent
Rose et al.

(10) Patent No.: US 6,174,530 B1
(45) Date of Patent: *Jan. 16, 2001

(54) HOMOGENEOUS POLYOXIME COMPOSITIONS AND THEIR PREPARATION BY PARALLEL ASSEMBLY

(75) Inventors: Keith Rose, Geneva; Robin Ewart Offord, Croix-de-Rozon, both of (CH)

(73) Assignee: Gryphon Sciences, South San Francisco, CA (US)

(*) Notice: Under 35 U.S.C. 154(b), the term of this patent shall be extended for 0 days.

This patent is subject to a terminal disclaimer.

(21) Appl. No.: 08/114,877

(22) Filed: Aug. 31, 1993

Related U.S. Application Data

(63) Continuation-in-part of application No. 08/057,594, filed on May 5, 1993, now abandoned.

(51) Int. Cl.[7] .................. A61K 39/395; A61K 51/00; G01N 33/53; C07K 1/00

(52) U.S. Cl. ................ 424/193.1; 424/1.11; 424/1.49; 424/178.1; 435/7.2; 530/345; 530/391.1; 530/403; 530/404; 530/405; 530/406; 530/408; 530/409; 530/410

(58) Field of Search ................. 530/345, 403, 530/404, 405, 406, 408–410, 391.1, 323; 424/178.1, 193.1, 1.49, 1.11; 435/7.2; 436/544; 526/19

(56) References Cited

U.S. PATENT DOCUMENTS

| | | |
|---|---|---|
| 4,444,744 | 4/1984 | Goldenberg . |
| 4,507,466 | 3/1985 | Tomalia et al. . |
| 4,622,420 | 11/1986 | Meares et al. . |
| 4,652,440 | 3/1987 | Paik et al. . |
| 4,659,839 | 4/1987 | Nicolotti et al. . |
| 4,678,667 | 7/1987 | Meares et al. . |
| 4,707,352 | 11/1987 | Staurianopoulos . |
| 4,857,599 | 8/1989 | Tomalia et al. . |
| 4,861,581 | 8/1989 | Epstein et al. . |
| 4,865,835 | 9/1989 | Begent . |
| 4,918,164 | 4/1990 | Hellstrom et al. . |
| 5,011,676 | 4/1991 | Thakur . |
| 5,084,266 | 1/1992 | McKenzie et al. ............ 424/9 |
| 5,087,616 | 2/1992 | Myers et al. ............... 514/21 |

FOREIGN PATENT DOCUMENTS

| | | |
|---|---|---|
| 0 131 361 | 1/1985 | (EP) . |
| 243 929 | 11/1987 | (EP) . |
| 0 339 695 | * 11/1989 | (EP) . |
| 0 498 771 | 8/1992 | (EP) . |
| 0 525 992 | 2/1993 | (EP) . |
| WO 85/05638 | 12/1985 | (WO) . |
| WO 90/02135 | 3/1990 | (WO) . |
| WO 91/13097 | 9/1991 | (WO) . |

OTHER PUBLICATIONS

Tam, J. & Zavala, F. "Multiple antigen peptide: A novel approach to increase detection sensitivity of synthetic peptides in solid–phase immunoassays" (1989) *J. Immunol. Methods* 124:52–61.

Drijfhout, J.W., and Bloemhoff, W. "A new synthetic functionalized antigen carrier" (1991) *Int. J. Peptide Protein Res.* 37:27–32.

Schnölzer, M., and Kent, S.B.H., "Constructing Proteins by Dovetailing Unprotected Synthetic Peptides: Backbone–Engineered HIV Protease" (1992) *Science* 256:221–225.

Goeghegan, K.F., and Stroh, J.G., "Site–Directed Conjugation of Nonpeptide Groups to Peptides and Proteins via Periodate Oxidation of a 2–Amino Alcohol. Application to Modification at N–Terminal Serine" (1992) *Bioconjugate Chem.* 3:138–146.

Gaertner, H.F., et al., "Construction of Protein Analogues by Site–Specific Condensation of Unprotected Fragments" (1992) *Bioconjugate Chem.* 3:262–268.

Reines, S.A., and Cantor, C.R., "New fluorescent hydrazide reagents for the oxidized 3'–terminus of RNA" (1984) *Nucleic Acids Res.* 1:767–786.

Murphy, A.M. et al., "Automated Synthesis of Peptide C–Terminal Aldehydes" (1992) *J. Amer. Chem. Soc.* 114:3156–3157.

Offord, R.E. in Protein Engineering: A Practical Approach— "Chemical approaches to protein engineering" (1992) *Rees, A.R. et al., eds., Oxford Press* pp. 235–251.

Hobbs et al., "Identification of a Lymphocyte–Activating Pentapeptide Sequence in the Fc Region of Human IgG1[1]" (1987) *J. Immunol.* 138:2581–2586.

Antoni et al., "A Short Synthetic Peptide Fragment of Human Interleukin 1 With Immunostimulatory But Not Inflammatory Activity" (1986) *J. Immunol.* 137:3201–3204.

(List continued on next page.)

* cited by examiner

Primary Examiner—Ponnathapu Achutamurthy
Assistant Examiner—Maurie E. Garcia
(74) Attorney, Agent, or Firm—Cooley Godward LLP

(57) ABSTRACT

Provided by this invention are essentially homogeneous, defined compositions of matter comprising a baseplate structure having a plurality of oxime bonds, wherein each oxime bond links a specifically active molecule to the baseplate. Also provided are novel baseplates having a plurality of oxime forming complementary reactive groups and novel specifically reactive molecules having an oxime forming complementary reactive group. Also provided by this invention are methods of preparing these novel compositions of matter by chemoselectively ligating via oxime bond formation a complementary orthogonal reactive group on the baseplate to a complementary reactive orthogonal group on a specifically active molecule. Methods of using these defined compositions of matter as well as pharmaceutical compositions comprising these defined compositions of matter and methods of their use are also provided by this invention.

18 Claims, 12 Drawing Sheets

OTHER PUBLICATIONS

Nencioni et al., "In Vivo Immunostimulating Activity of the 163–171 Peptide of Human IL–1β" (1987) *J. Immunol.* 139:800–804.

Brinkley, M., "A Brief Survey of Methods for Preparing Protein Conjugates with Dyes, Haptens, and Cross–Linking Reagents" (1992) *Bioconj. Chem.* 3:2–13.

King et al "Preparation of Protein Conjugates via Intermolecular Hydrazone Linkage" (1986) *Biochemistry* 25:5774–5779.

Mutter et al., "The Construction of New Proteins: V.A. Template–Assembled Synthetic Protein (TASP) Containing Both a 4–Helix Bundle and β–Barrel–Like Structure" (1989) in *Proteins: Structure, Function & Genetics* 5:13–21.

Argos, P., "An Investigation of Oligopeptides Linking Domains in Protein Tertiary Structures and Possible Candidates for General Gene Fusion" (1990) *J. Mol. Biol.* 211:943–958.

Altmann, K.H. & Mutter, M., "A General Strategy for the De Novo Design of Proteins–Template Assembled Synthetic Proteins" (1990) *Int. J. Biochem.* 22:947–956.

Floegel et al., "Molecular Dynamics Conformational Search of Six Cyclic Peptides Used in the Template Assembled Synthetic Protein Approach for Protein De Novo Design" (1992) *Biopolymers* 32:1283–1310.

Moore, J.S., "Carborod Molecular Scaffolding" (1993) *Nature* 361:118–119.

Rana et al., "Synthesis of A Metal–Ligating Amino Acid Suitable for Solid Phase Assembly of Peptides" (1992) *Tetrahedron Lett.* 33:4521–4524.

Kaneko et al., "New hydrazone Derivatives of Adriamycin and Their Immunoconjugates–a Correlation between Acid Stability and Cytotoxicity" (1991) *Bioconj. Chem.* 2:133–141.

Pochon et al., "A Novel Derivative of the Chelon Desferrioxamine for Site–Specific Conjugation to Antibodies" (1989) *Int. J. Cancer* 43:1188–1194.

Ryser et al., "Colon Carcinoma Immunoscintigraphy by Monoclonal Anti–CEA Antibody Labeled with Gallium–67–Aminooxyacetyldeferroxamine" (1992) *J. Nucl. Med.* 33:1766–1773.

Kurth et al., "Site–Specific Conjugation of a Radioiodinated Phenethylamine Derivative to a Monoclonal Antibody Results in Increased Radioactivity Localization in Tumor" (1993) *J. Med. Chem.* 36:1255–1261.

Rose et al., "Attachment of Linker Groups to Carboxyl Termini Using Enzyme–Assisted Reverse Proteolysis" (1989) in *Peptides 1988*, G. Jung & E. Bayer (eds.) Walter de Gruyter, Berlin–New York pp. 274–276.

Fisch et al., "Site–specific modification of antibodies by enzyme–assisted reverse proteolysis" (1991) in *Peptides 1990*, E. Giralt & D. Andreu (eds.) ESCOM Science Publishers B.V., The Netherlands pp. 819–821.

Rose et al., "Site–Specific Modification of Natural and Biosynthetic Polypeptides by Reverse Proteolysis" (1992) *Innovation and Perspectives in Solid Phase Synthesis*, R. Epton (ed.) Intercept., Andover 1992 pp. 129–134.

Offord, R.E., "Chemical Approaches to Protein Engineering" (1990) in *Protein Design and the Development of New Therapeutics and Vaccines*, J.B. Hook & G. Poste (eds.) The British Library, Plenum, New York pp. 253–282.

Biancalana et al., "Tactics and Strategies in Solid Phase Peptide Synthesis: New Directions, Methods and Applications" (1992) in *Innovation and Perspectives in Solid Phase Sunthesis*, R. Epton (ed.) Intercept Limited, Andover 1992 pp. 135–152.

Marsden and Subak–Sharpe, "Preparation of branched peptides in assays for antibodies" (1993) *Chem. Abs.* 118:234487w.

Defoort et al., "A rational design of synthetic peptide vaccine with a built–in adjuvant" (1993) *Chem. Abs.* 118:231792f.

Williams, R.E. "Monitoring multiple antigen peptide (MAP) syntheses and peptide reorientation of a new MAP core" (1993) in *Peptides 1992*, C.H. Schneider & A.N. Eberle (eds.) ESCOM Science Publishers B.V. Canada pp. 911–912.

Dawson, P.E. and Kent, S.B.H., "Convenient Total Synthesis of a 4–Helix TASP Molecule by Chemoselective Ligation" (1993) *J. Amer Chem. Soc.* 115:7263–7266.

Mutter et al., "Redesigning peptide structures: Side–chain assemblage on topological templates" (1993) in *Peptides 1992*, C.H. Schneider & A.N. Eberle (eds.) ESCOM Science Publishers B.V., The Netherlands pp. 87–88.

Kaumaya et al., "Template vaccine strategy bypasses haplotype–restricted immune responses" (1993) in *Peptides 1992*, C.H. Schneider & A.N. Eberle (eds.) ESCOM Science Publishers B.V., Colmbus, OH pp. 139–141.

Houghton et al., "Development of New Antimicrobial Agents Using a Synthetic Peptide Combinatorial Library Involving More Than 34 Million Hexamers" (1992) *Innovation and Perspectives in Solid Phase Synthesis* R. Epton (ed.) Intercept Limited, Andover pp. 237–239.

Tomalia et al., "Starburst Dendrimers: Molecular–Level Control of Size, Shape, Surface Chemistry, Topology, and Flexibility from Atoms to Macroscopic Matter" (1990) *Angew. Chem. Int. Ed. Engl.* 29:138–175.

Vilaseca et al., "Synthesis and use of a defined oligomer for targeted drug therapy" (1993) in *Peptides 1992*, C.H. Schneider & A.N. Eberle (eds.) ESCOM Science Publishers B.V., Geneva, Switzerland pp. 819–820.

Tuchscherer et al., "Protein De Novo Design: Condensation of Unprotected Peptide Blocks to Topological Templates via Selective Oxime Bond Formation" (Jun. 1993) 13th American Peptide Symposium, Edmonton, Canada Abstract P976.

Ernest et al., "Synthesis of A 4–Helix Bundle–Like Template–Assembled Synthetic Protein (TASP) by Condensation of a Protected Peptide on a Conformationally Constrained Cyclic Carrier" (1990) *Tetrahedron Letters* 31(28):4015–4018.

Robey, F.A. and Fields, R.L., "Automated Synthesis of N–Bromoacetyl–Modified Peptides for the Preparation of Synthetic Peptide Polymers, Peptide–Protein Conjugates, and Cyclic Peptides" (1989) *Analytical Biochemisstry* 177:373–377.

Tam et al., "Incorporation of T and B Epitopes of the Circumsporozoite Protein in a Chemically Defined Synthetic Vaccine Against Malaria" (1990) *J. Exp. Med.* 171:299–306.

Tam, J.P., "Synthetic peptide vaccine design: Synthesis and properties of a high–density multiple antigenic peptide system" (1988) *Proc. Natl. Acad. Sci. USA* 85:5409–5413.

Defoort et al., "Complete synthetic vaccine with built–in adjuvant" (1992) in *Peptides 1991*, J.E. Rivier (ed.) ESCOM Leiden, New York pp. 845–846.

Posnett et al., "A Novel Method for Producing Anti–peptide Antibodies: Production of Site–Specific Antibodies to the T Cell Antigen Receptor β–Chain" (1988) *The Journal of Biological Chemistry* 263(4):1719–1725.

Mueller et al., (1990), Biconjugate Chem., 1:325–330.

Webb, et al., (1990), Bioconjugate Chem., 1:96:99.

Roberts et al (1990) "Using Starburst Dendrimers as Linker Molecules to Radiolabel Antibodies", Bioconjugate Chemistry 1(5): 305–308.*

NOCH₂CO-ELGGGPGAGSLQPLALEGSLQKR-OH
                    ‖
CHCO-G G G K K K K G-OH

-COCH=NOCH₂CO-ELGGGPGAGSLQPLALEGSLQKR-OH
-COCH=NOCH₂CO-ELGGGPGAGSLQPLALEGSLQKR-OH
-COCH=NOCH₂CO-ELGGGPGAGSLQPLALEGSLQKR-OH
-COCH=NOCH₂CO-ELGGGPGAGSLQPLALEGSLQKR-OH
-COCH=NOCH₂CO-ELGGGPGAGSLQPLALEGSLQKR-OH

FIG. 7

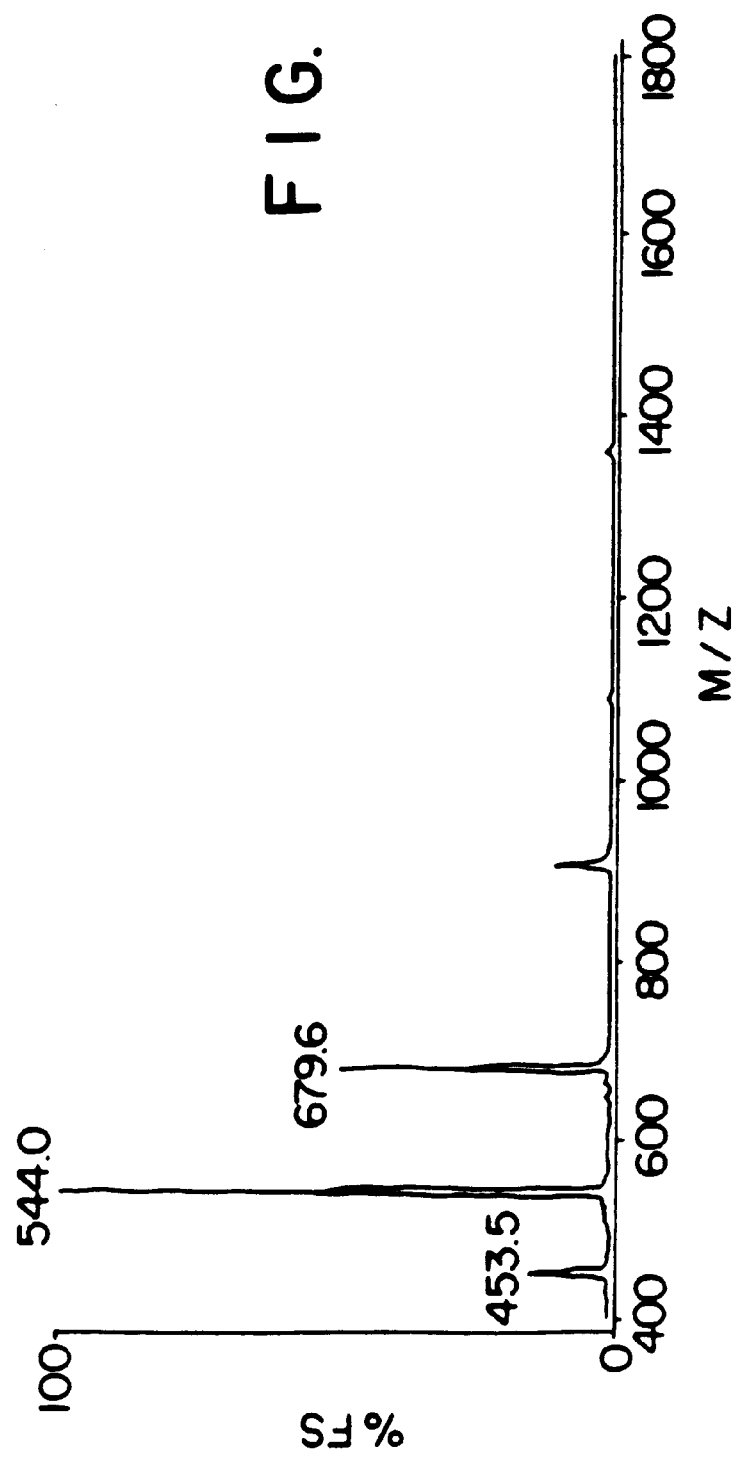

HOMOGENEOUS POLYOXIME COMPOSITIONS AND THEIR PREPARATION BY PARALLEL ASSEMBLY

CROSS-REFERENCE TO RELATED APPLICATIONS

This application is a continuation-in-part of U.S. application Ser. No. 08/057,594, filed May 5, 1993, now abandoned which is incorporated herein by reference.

INTRODUCTION

1. Technical Field

The invention relates generally to homogeneous preparation of macromolecules of defined structure containing a plurality of linkages and to reagents and methods for assembly of such molecules.

2. Background

Two methods have traditionally been used to produce complex polymers such as polypeptides. One method relies on relatively uncontrolled polymerization reactions, wherein monomer subunits react to produce large polymers. Using this method, polydisperse macromolecules such as polypeptides and plastics (e.g., polyethylene or nylon) can be produced from monomeric residues such as amino acids or small aliphatic or aromatic organic molecules, respectively. While such polydisperse macromolecules can be relatively easy to produce, the polymeric macroscopic products are not homogeneous at the molecular level but are mixtures of polymers of different lengths and even different composition, e.g., in a random copolymer). Furthermore, the similarity of the homologs produced in such polydisperse preparations makes it difficult or impossible to obtain a single high molecular weight product in pure form.

The second method utilized to obtain complex macromolecules has been the sequential assembly of reversibly protected monomers. This approach can be used to obtain products of defined, typically linear, structure. Unfortunately, the method is limited in the size and, most critically, the complexity of molecules that can be produced. For example, synthesis of defined polypeptides or proteins larger than about 50–80 amino acid residues has been beyond the reach of this technology. Condensation of pre-purified protected peptides, two at a time, is limited by the insolubility of large protected fragments. As a result, synthesis of homogeneous, linear polypeptides, for example, is limited to an upper limit of about 100 amino acid residues.

Mutter et al. (Proteins:Structure, Function and Genetics (1989) 5:13–21) have synthesized branched chain polypeptides by step-wise coupling of protected amino acids to a synthetic, protected, resin-bound peptide template during solid-phase peptide synthesis. Deprotection and cleavage was required to obtain a soluble template-assembled synthetic protein. Also using step-wise, solid phase peptide synthesis, Tam and Zavala (J. Immunol. Meth. (1989) 124:52–61) have built branched chain "lysine tree" templates with peptide branches, referred to as multiple antigen peptides, which were subsequently obtained in soluble, crude form after HF deprotection and cleavage.

Since protecting groups used in polypeptide synthesis generally decreases solubility of the protectable molecule, the ability to condense unprotected polypeptides would provide an improvement in the solubility problem encountered using protected precursors, as well as, minimize harsh deprotection methods needed to achieve a final product. However, the use of unprotected precursors raises the seemingly insurmountable problem of regiospecificity. Therefore, attempts have been made to use regiospecific condensation of unprotected fragments through the use of chemoselective ligation.

Chemoselective ligation requires the use of complementary pairs of reactive groups present at specific sites on the precursor molecules that are being joined. The use of reactive groups having complementary chemical reactivity, such as a thiol group and a bromoacetyl group, results in the formation of a bond in a regiospecific manner. For example, thiol-type chemoselective ligations have been used to prepare a multi-antigenic peptides. In an attempt to avoid harsh deprotection methods and formation of impure products caused by possible steric hindrance between closely spaced growing peptide arms during step-wise solid phase synthesis, Drijfhout and Bloemhoff (*Int. J. Peptide Protein Res.* (1991) 37:27–32) used thiol-type chemoselective coupling by synthesizing a branched "octa-lysine tree" peptide, whose deprotected epsilon amino groups were extended to contain protected sulfhydryl groups (S-acetylmercaptoacetyl) for subsequent coupling to an appropriately modified sulfhydryl-containing antigenic peptide. However, the product obtained had poor characteristics as defined by high performance liquid chromatography and was not fully characterized. More recently, thiol chemistry was used to prepare, in a two-fragment condensation, a totally synthetic, linear, functional HIV protease analog (Schnolzer and Kent (1992) Science 256:221–225).

Unfortunately, thiol chemistry is not completely specific. It is well known, for example, that thiol groups can participate in disulfide bond shuffling. In addition, alkylating agents such as bromoacetyl and maleoyl can react with nucleophilic amino acid groups other than a thiol group. For example, bromoacetyl can react with the thioether side chain of methionine residues, thus limiting the homogeneity and/or complexity of design of the desired product.

Thus, a need exists for homogeneous preparations of easily synthesized homogeneous macromolecules of defined structure having stable ligation linkages and for reagents and methods for constructing these homogeneous preparations of macromolecules that provide ease, rapidity and mildness of synthesis; essentially quantitative yields; versatility in template design; and applicability to construction using a diversity of biochemical classes of compounds. In addition a need exists for homogeneous macromolecules of defined structure that can be designed for desired activity, solubility, conformation and other desirable properties; that present components, such as peptides or oligonucleotides, in non-linear, polyvalent form; that provide higher binding affinity and specificity of interaction; and that are available as homogeneous preparations. The present invention satisfies these needs and provides related advantages as well.

SUMMARY OF THE INVENTION

The present invention is directed to homogeneous preparations of easily synthesized, homogeneous molecules of defined structure containing a plurality of stable oxime linkages formed by parallel assembly and to reagents and methods for rapid and specific parallel assembly of such molecules by chemoselective ligation via oxime formation.

The macromolecules of defined structure comprise an organic molecule to which other molecules will become attached (referred to as a baseplate) having a plurality of oxime linkages, preferably at least three, linked in the same orientation to a plurality of a second organic molecule. Also provided are two reagents for constructing these molecules:

baseplates having a plurality of oxime-forming reactive groups and a second organic molecule having an orthogonal reactive group complementary in oxime linkage formation to the oxime forming orthogonal reactive groups present on the baseplate. For the purposes of the present invention, the second organic molecules are alternatively referred to as complementary orthogonal specifically active molecules ("COSM") and are defined further below. The oxime linkages provide a hydrolytically stable means of joining oligomer or macromolecule subunits. The various reactive groups are referred to herein as "orthogonal" groups, which means that are complementary to each other in reactivity and do not react with other functional groups present in the precursors of the macromolecule being formed.

Also provided by this invention are methods of preparing these molecules by parallel self-assembly comprising chemoselectively linking each of a plurality of orthogonal reactive groups on a baseplate to its complementary reactive orthogonal group present on one of a plurality of a second organic molecule via oxime bond formation. The baseplate and second organic molecules are preferably formed from amino acid resides. In other embodiments, baseplates and/or second organic molecules are formed from or further comprise sugar residues, nucleic acid residues and/or lipids. Preferred baseplates are prepared by controlled, organic chemical syntheses, such as solid phase peptide synthesis ("SPPS") or the equivalent for nucleic acid or sugar-containing baseplates. Homogeneous preparations of isolated peptides or proteins (prepared for example by recombinant means) are also suitable for use in making baseplate embodiments; however, such molecules must be designed or chosen to contain residues compatible with subsequent regio-specific modification to obtain a plurality of oxime-forming orthogonal reactive groups, and, in addition, maintain a defined structure and significant homogeneity after the regio-specific modification. Accordingly, heterogeneous antibody glycoprotein preparations subsequently modified by chemical or enzymatic oxidation of sugar residues are not suitable baseplate embodiments of the present invention.

Methods of using these parallel assembled polyoxime compounds are also provided, including use as antigens and immunogens. Pharmaceutical compositions comprising these compositions of matter are provided. Kits providing polyoximes of the invention or reagents for their synthesis are provided.

The polyoxime compounds of the invention are relatively complex, synthetically prepared macromolecules. The most massive species prepared to date is an approximately 20 kD complex, containing 195 amino acid residues: the octa-oxime formed between $NH_2OCH_2CO$-ELGGGPGAGSLQPLALEGSLQKR-OH (SEQ ID NO:10) and $O=CH$-CO-$Gly_3$-[Lys(COCHO)]$_7$-Gly-OH (SEQ ID NO:9). As will be apparent to those skilled in the art in the light of this disclosure, even larger and more complex molecules are now readily accessible in homogeneous and defined form given the rapid, specific, high-yielding, mild and versatile methods of preparing these compounds provided by this invention.

BRIEF DESCRIPTION OF THE DRAWINGS

FIG. 7 depicts the structure of the hexa-Pep C-polyoxime. As indicated, a Pep C-COSM is attached to each of the five ε-positions of the lysine residues in the baseplate structure and to the N-terminus of the baseplate structure.

FIG. 12 shows the mass spectra and calculated molecular weight obtained by electrospray ionization mass spectrometry of the homo-polyoxime formed between the baseplate terephthalaldehyde and the peptide $NH_2OCH_2CO$-Nle-Asp-His-(D-Phe)-Arg-Trp-Lys-OH (a synthetic analog of alpha-melanocyte stimulating hormone ("MSH").

DETAILED DESCRIPTION OF THE INVENTION

Definitions

Figure 1:
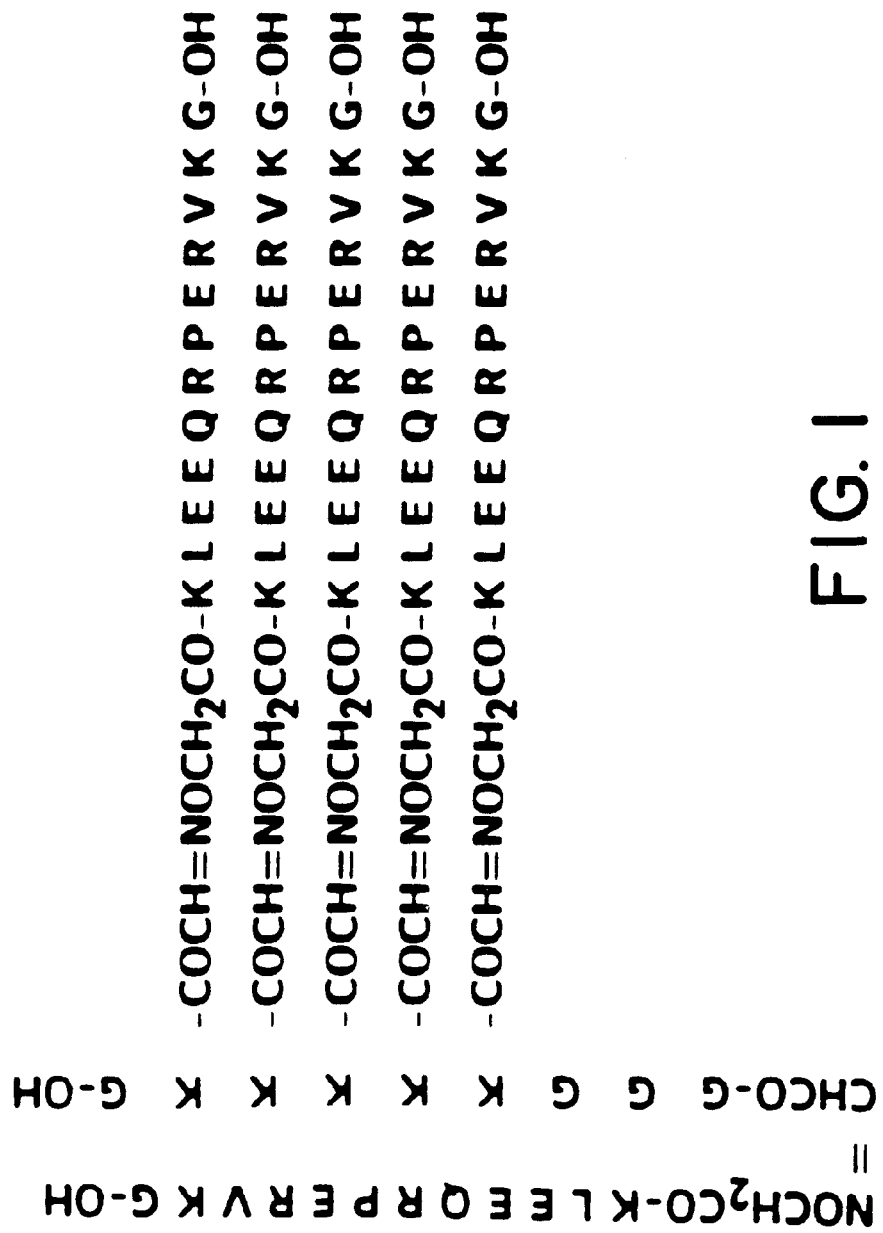
FIG. 1 depicts the structure of the hexa-TCTP-polyoxime. As indicated, a TCTP-COSM is attached to each of the five ε-positions of the lysine residues in the baseplate structure and to the N-terminus of the baseplate structure.

For the purpose of this invention, the following terms are defined as follows.

A "complementary orthogonal chemically reactive group" is defined as one of a pair of chemically reactive groups that chemospecifically reacts with the complementary member of the pair. For example, amino-oxy-acetyl ("AOA") and glyoxylyl ("GXL") are complementary orthogonal chemically reactive groups that react to form an oxime bond.

The term "chemoselectively ligated" indicates the specific ligation that occurs between complementary orthogonal chemically reactive groups.

"Orthogonal" refers to conditions or groups which can be used without compromising other groups present or other chemistry to be applied. Thus, by way of example, in the context of this application, amino-oxy-acetyl groups are orthogonal.

A "complementary orthogonal specifically active molecule" ("COSM") is a molecule containing a complementary orthogonal chemically reactive group and a specifically active molecule or portion thereof. A COSM is defined in part by having a complementary orthogonal chemically reactive group capable of chemoselective ligation to the complementary orthogonal chemically reactive group present on a baseplate structure. For purposes of the present invention, the complementary orthogonal chemically reactive group of a COSM must be one member of an oxime-linkage-forming reactive pair. The term "specifically active" indicates that the COSM also has a defined biological, chemical or physical activity apart from its complementary orthogonal chemical reactivity. It is of course apparent that a defined, inherent activity for a COSM may not be immediately apparent from the COSM structure itself before reaction with the baseplate to form the final macromolecule product. As such the term COSM is not meant to limit the nature of the second organic molecules and is meant to be used interchangeably therewith. Furthermore, any specific activity associated with the second organic molecule can be activated or realized after attachment to the baseplate.

"Specific biological activity" means a biological activity imparted to a particular molecule or group by virtue of its structure. A specific biological activity can be unique to the particular molecule or group or can be associated with the members of a family to which the particular molecule or group.

One skilled in the art would know that a specific biological activity also can be associated with structurally dissimilar or unrelated molecules or groups that possess the same specific biological activity as a particular molecule or group. For example, an anti-idiotypic antibody can have the same specific biological activity as the antigen used to raise the antibody to which the anti-idiotypic antibody was raised, even though the anti-idiotypic antibody and the antigen are structurally dissimilar.

"Specific chemical reactivity" means a chemical activity imparted to a particular molecule or group by virtue of its structure. A specific chemical activity can be unique to the particular molecule or group or can be associated with the members of a family to which the particular molecule or group. Alternatively, a specific chemical activity can be associated with a small number of structurally dissimilar or unrelated molecules or groups that posses the same specific chemical activity as a particular molecule or group.

"Parallel assembly" means the multi-site, controlled reaction that occurs when a plurality of a second organic molecules (COSMs) having one type of orthogonal chemically reactive group chemoselectively ligate to the complementary orthogonal chemically reactive groups on the baseplate structure.

An antigenic molecule encompasses a substance, frequently RNA or a peptide, that can stimulate an animal organism to produce antibodies and that can combine specifically with the antibodies thus produced. An antibody-antigen complex means a molecular aggregate that is formed by the specific interaction of antigens and antibodies.

An antibody is a glycoprotein of the globulin type that is formed in an animal organism in response to the administration of an antigen and that is capable of combining specifically with the antigen. These are also referred to as immunoglobulins. Antibody fragments can retain some ability to selectively bind with their antigen or hapten. The ability to bind with an antigen or hapten is determined by antigen-binding assays (see, for example, *Antibodies: A Laboratory Manual*, Ed Harlow et al., eds., Cold Spring Harbor, N.Y. (1988), which is incorporated herein by reference). Such antibody fragments include, but are not limited to, Fab, Fab' and (Fab')$_2$. A native antibody is one which is isolated from an animal or from an animal or hybrid animal (hybridoma) cell line.

A hapten refers to the portion of an antigen that reacts with the immune products of an immune response, but cannot by itself induce an immune response without being complexed to a carrier to form the complete antigen. Metal chelates are one example of a hapten.

As used herein, "complementarity determining region" (CDR) refers to amino acid sequences on either the variable light and variable heavy chains of an antibody which form a three-dimensional loop structure that contributes to the formation of the antigen or hapten binding site.

A therapeutic agent is any molecule, which, when administered to an animal, prevents or alleviates a disease or arrests or alleviates a disease state in the animal. Therapeutic agents may include, but are not limited to, antitumor antibiotics, antiviral proteins, radioisotopes, pharmaceuticals or a toxin.

A multivalent molecule is a molecule having more than one binding site for interaction between molecules. An example of a multivalent molecule is a polyvalent immunogen that contains multiple antigens.

A "pharmaceutically acceptable carrier" means any of the standard pharmaceutical carriers, such as a phosphate buffered saline solution; water; or emulsion, such as an oil/water emulsion; potentially including and various types of wetting agents.

Administered means providing the subject with an effective amount of the compound or pharmaceutical composition. Methods of administration to an animal are well known to those of ordinary skill in the art and include, but are not limited to, oral, intravenous, transdermal, and parenteral administration. Administration may be effected continuously or intermittently throughout the course of other treatments. Methods of determining the most effective means and dosage of administration are well known to those of still in the art and will vary with the compound or composition for treatment, the purpose of therapy and the animal or patient being treated.

A peptide or protein shall mean both naturally occurring and recombinant forms, as well as other non-naturally occurring forms of the peptide or protein which are sufficiently identically to the naturally occurring peptide or protein to allow possession of similar biological or chemical activity. As is known in the art peptides can be formed from of non-naturally occurring or non-proteinogenic amino acid residues. Furthermore, as is well known in the art, amino acid residues can be joined via non-amide linkages. Peptides or proteins can also contain protecting groups at either terminal that prevent or minimize degradation of the peptide or protein in vivo.

A "homogeneous polyoxime composition" of the invention refers to a chemical composition in which substantially all of the polyoxime molecules have identical chemical structures (in contrast to a typical organic polymer in which the individual molecules differ at least in length and often in specific structure, as in a random copolymer). Such compositions can also be referred to as "self-identical" compositions, as substantially all of the individual molecules of the polyoxime are identical to each other. Here "substantially all" refers to at least 80% of the total baseplate molecules all having the same number of identical COSMs attached to the baseplate. Increasing degrees of purity, such as 90%, 95%, 98%, 99%, 99.5%, 99.8%, etc., all the way to 100%, are increasingly preferred meanings of "substantially all."

A "macromolecule" as used herein refers to an organic molecule (which includes molecules of biologic origin as well as organic molecules with inorganic components) having a molecular weight of at least 2000, preferably at least 5000, more preferably at least 10,000.

Description

This invention provides novel, multivalent molecules of defined structure comprising a plurality of stable oxime linkages, homogeneous compositions of these molecules, and reagents and methods for rapid and specific parallel assembly of such molecules by chemoselective ligation via oxime formation. For purposes of this invention these molecules are referred to generally as polyoximes.

The polyoxime compounds comprise an organic baseplate molecule having a plurality of oxime linkages, preferably at least three, to a plurality of a second organic molecule with all oxime linkages in the same orientation. Baseplates are organic molecules having a plurality of an oxime-forming orthogonal reactive group which can react chemoselectively with its complementary orthogonal reactive group present on any one of a plurality of a second organic molecule. Homogeneous compositions of polyoximes are formed by reaction via oxime bond formation of a complementary orthogonal reactive group on a baseplate to its complementary orthogonal reactive group on a second specifically active molecule. In a preferred embodiment of the invention, the baseplate structure is a peptide having a backbone formed from amino acid residues. As is known in the art, peptides containing non-naturally occurring amino-acids or D-optical isomers or substituted (e.g. N-substituted) amino acids, β-amino acids, or the like, can be made by chemical synthesis; peptides containing uncommon amino acids can be made by recombinant means but are usually produced by chemical synthesis or post-expression modification. The peptide baseplate backbone comprises amino acid residues having side-chain groups suitable for modification during peptide synthesis to oxime-forming complementary orthogonal reactive groups. Chemically reactive groups that can form oxime linkages with a complementary chemically reactive group on a COSM are present on at least three of the amino acid residues in the baseplate. Amino acid residues can be incorporated during peptide bond formation as modified monomers containing oxime-forming chemically reactive groups or can be modified after formation of peptide bonds to contain such groups. Preferred common residues to carry oxime forming groups can be those which are available in differentially protected form, can easily be modified by conventional methods and which give stable derivatives. Preferred are lysine and ornithine residues, which are very easily acylated and can be modified by reductive alkylation. Less preferred residues are serine, threonine, histidine, methionine (which can be alkylated), tyrosine (which can be alkylated but whose acyl derivatives are not very stable), and tryptophan (which can be alkylated but whose acyl derivatives are unstable). Residues can also be selected for conferring desired physical or biological properties, e.g. such as spacing, charge, solubility. Also preferred residues to carry an oxime forming group are homologs of these amino acids, D rather than L isomers, substituted derivatives (e.g. N-substituted), and β-amino acids.

Other embodiments contain baseplates and/or COSMs formed in whole or part from sugar residues, nucleic acid residues and/or lipids. As will be apparent from the disclosure of this invention, almost any oligo- or macromolecule building block residue can be used to form a COSM or a baseplate. As will be apparent to those in the art in the light of this disclosure, even larger and more complex molecules are now readily accessible given the rapid, specific, high-yielding, mild and versatile methods of preparing these compounds.

In one embodiment the baseplate or COSM is designed and prepared by recombinant methods or isolated from natural sources, and an oxime-forming complementary orthogonal reactive group, such as an aldehyde, is site-specifically formed on the C-terminal of the polypeptide by selective enzyme catalyzed reverse proteolysis or at an N-terminal serine or threonine by mild oxidation. (See for example Geoghegan et al. (Bioconjugate Chem. (1992) 3:138–146), Gaertner et al. (Bioconjugate Chem. (1992) 3:262–268), EP 243929, and WO 90/02135 which are incorporated herein by reference.) For use as a multivalent baseplate, a homogeneous preparation of recombinant or natural peptide preferably has multiple C-or N-termini, such as would occur in a dimer or tetramer, for ease of specific formation of orthogonally reactive groups. For example an insulin analog having an A chain covalently linked to a B chain, each chain having an N-terminal serine (or threonine), can be converted to a divalent aldehyde baseplate by regioselective oxidation. In a further embodiment, the C-termini can be modified by enzyme catalyzed reverse proteolysis to create a tetra-aldehyde baseplate. Such baseplates have at least the advantages of size and complexity over solid phase synthesis peptide baseplates. As is taught herein a great flexibility is available to one in the art for designing and obtaining baseplates and COSMs of desired sequence, structure and function with specifically placed complementary reactive groups.

Although the preferred baseplate and COSM structures are typically formed from amino acid residues, other embodiments can be formed from further comprise sugar residues, nucleic acid residues and/or lipids.

Where the baseplate or COSM structure is a peptide, the terminal chemical groups are normally an amino group and a carboxy group. One skilled in the art will know that these terminal groups can be made reactive or unreactive. Unreactive groups can be unreactive because the group is chemically protected and can be made reactive by deprotecting or otherwise modifying the group as taught herein and as is known in the art. Alternatively, the terminal chemical groups of a baseplate can be covalently bonded to a residue within the baseplate structure to create a cyclic baseplate structure.

This invention provides in one embodiment a baseplate structure in which one complementary reactive group capable of oxime-linkage formation is an amino-oxy group or an aldehyde group. Preferred are amino-oxy-acetyl ("AOA") or aldehyde groups such as OHC—CH— or glyoxylyl ("GXL"). In fact, additional structure (X in the formula) can be used which connects an aldehyde group (or an amino-oxy group) to a structure of interest: e.g., OCH-X-Nle-Asp-His-(D-Phe)-Arg-Trp-Lys-OH, where X can simply be —CO— or a more elaborate structure; or $NH_2$-O-X-Nle-Asp-His-(D-Phe)-Arg-Trp-Lys-OH, where X can simply be —$CH_2$—CO— or a more elaborate structure.

For aldehyde baseplates, functional groups present in the additional connecting structure adjacent to the aldehyde function are not critical; however, a requirement of these groups is that they do not interfere with the formation of the oxime linkage between the aldehyde and its complementary amino-oxy group. They should not react in preference to the aldehyde group with the amino-oxy, nor provide steric hindrance to the reaction, nor deactivate the reactive groups. The connecting group preferably represents a non-reacting group comprising substituted or unsubstituted aliphatic or aromatic groups such as phenyl or $C_1$–$C_{10}$ alkylene moieties, $C_1$–$C_{10}$ alkyl groups, or a combination thereof, or an amino acid chain (such as a flexible hinge or loop sequence (see for example Argos, *J. Mol. Biol.* (1990) 211:943–958), or a nucleotide chain or a sugar chain or a lipid chain or a combination thereof and may contain heteroatoms.

For amino-oxy baseplates, functional groups present in the additional connecting structure adjacent to the amino-oxy function are not critical; however, a requirement of these linking groups is that they do not interfere with the formation of the oxime linkage between the amino-oxy and its complementary aldehyde group. They should not react in preference to the amino-oxy group with the aldehyde, nor provide steric hindrance to the reaction, nor deactivate the reactive groups.

The foregoing discussion describing functional groups present in the additional connecting structure adjacent to the aldehyde function or the amino-oxy function present on baseplates applies to connecting groups on COSMs.

Where the polyoxime is to be used for antigenic or immunogenic purposes, it is apparent to one skilled in the art that connecting groups are chosen that are not strongly immunogenic.

The hydrolytic stability of oximes is influenced by their structure; data indicate that oxime stability increases in the series: —CO—NH—$CH_2$—CH=N—O—$CH_2$—<—NH—CO—CH=N—O—$CH_2$—<—$C_6H_4$—CH=N—O—$CH_2$—.

Baseplates of the invention also optionally comprise residues that are not capable of forming oxime linkages with a COSM. Such residues can provide sufficient spacing between complementary reactive groups as to accommodate large COSMs. In addition such residues, when appropriately located, can provide other desirable features as are known or can be determined for sequences of such residues, including but not limited to providing desired tertiary conformation, conformational constraint, sidedness (as by formation of an amphipathic helix), scaffolding (as provided by engineered polypeptide minibodies), increased solubility, lipophilicity, biological activity or function. Examples of such chemically inert residues include but are not limited to amino acids, sugars and nucleotides. One skilled in the art is well aware of the various methods for predicting secondary and even tertiary structure of complex molecules techniques which are applicable to designing baseplate embodiments of the invention having desired functionality.

Where the baseplate structure comprises a peptide, one skilled in the art would know that the peptide baseplate structure will have a conformation in solution that depends in part on the amino acid sequence of the peptide. Such information is useful in determining an optimal amino acid sequence of the peptide baseplate structure for a specific task. For example, a peptide baseplate structure that is predicted to form an α-helix structure can be synthesized such that the amino acid residues that contain the complementary orthogonal chemically reactive groups extend from the same face of the α-helix. Following chemoselective ligation with a COSM, the specifically active region of each COSM will extend in the same direction. One skilled in the art knows of other types of conformations assumed by specific peptides in solution and therefore can synthesize polyoximes having desired tertiary structure, including desired spacing between adjacent COSMs. For example, preferred synthetic peptide baseplates, peptide design methods, and other synthetic considerations are exemplified in part by Altmann and Mutter (*Int. J. Biochem.* (1990) 22:947–956) and references cited therein.

A "lysine tree" formed by solid phase peptide synthesis as illustrated by Tam and Zavala (*J. Immunol. Meth.* (1989) 124:52–61), which is incorporated herein by reference, is suitable for use in baseplate formation if modified as described herein to contain oxime-forming complementary orthogonal reactive groups of the same orientation. Alternatively, a baseplate structure can be formed from a template such as used for "template assembled synthetic protein" ("TASP") described, for example, by Floegel et. al. (*Biopolymers* (1992) 32:1283–1310), which is incorporated herein by reference, if modified as described herein to contain oxime forming complementary orthogonal reactive groups of the same orientation. Aldehyde or amino-oxy end-functionalized carborods can serve as di-valent baseplates or alternatively COSMs. Carborods, which are prepared as homogeneous molecules of discrete length and defined structure, can be modified with specific end-group functionality. (See Moore, *Nature* (1993) 361:118–119, and references cited therein, which are incorporated by reference.)

When the baseplate is formed from amino acids, the peptide sequence of a baseplate structure can be synthesized by routine solid phase peptide synthesis ("SPPS") and, while the peptide is still attached to the solid phase, Boc-amino-oxyacetic acid (Boc-AOA) in an activated form such as the N-hydroxysuccinimide ester can be added to the nascent peptide chain. For example, the baseplate structure can consist of a peptide having five reactive groups such as five lysine residues. Boc-AOA N-hydroxysuccinimide ester can react with each of the ε-amino groups of the lysine residues, as well as the N-terminus α-amino group if left unprotected, to form the baseplate structure which, in this example, would contain an ε-AOA-pentalysine sequence and an AOA group at the N-terminus, if the N-terminus α-amino group was intentionally acylated.

Alternatively, Boc-serine(benzyl)-OH in an activated form such as the N-hydroxysuccinimide ester can be used to form the complementary orthogonal chemically reactive group on the baseplate structure. Boc-serine(benzyl) N-hydroxysuccinimide ester reacts with the ε-amino groups of the five lysine residues, as well as the N-terminus α-amino group if desired, to form a precursor baseplate containing ε-Ser-pentalysine and an N-terminus α-Ser group. Treatment of the precursor baseplate with a mild oxidizing agent, such as periodate at pH 7, will convert ε-Ser-pentalysine and, if present, the α-Ser-N-terminus to ε-GXL-pentalysine and an α-GXL-N-terminus, respectively, thus producing a hexa-GXL-baseplate structure.

The oxidation reaction can be terminated using any 1,2-diol or 1-amino-2-ol or 1-ol-2-amino compound having relatively free rotation about the 1,2 bond, such as ethylene glycol. Alternatively, the oxidation reaction can be terminated by rapid removal of periodate, for example by reverse phase high performance liquid chromatography (RP-HPLC). Since the oxidation reaction only occurs with serine residues containing a primary amino group, only the ε-serine residues and serine residues at the N-terminus of the peptide are converted to the glyoxylyl. One skilled in the art knows of methods for chemically protecting an N-terminal serine from oxidation, if such protection is desirable.

Following conversion of the ε- and α-serine residues to GXL groups, an oximation reaction can occur between the GXL-baseplate structure and complementary AOA-COSMs in the presence of periodate at pH 4.6 to form a polyoxime. Oximes form over a wide range of pH values and form rapidly at pH values less than about pH 5. The extent of polyoxime formation can be monitored by RP-HPLC and the reaction can be terminated by preparative RP-HPLC. The molecular weight of the resulting compound can be determined by electrospray ionization mass spectrometry. Alternatively, an AOA-baseplate structure can be used, and an oximation reaction can occur between the AOA-baseplate structure and a plurality of a COSM having an aldehyde group.

Alternatively, oximation is run at pH below 4.6. Lower pH can be advantageous for the solubility of some peptides. A pH of 2.1 is preferred for increasing the solubility of some peptides, e.g. amino-oxy-acetyl-YREDGVTPYMIFFKDGLEMEK-OH (SEQ ID NO:2). In addition oximation occurs much faster at pH 2.1 than at pH 4.6. One skilled in the art can determine the pH versus solubility profile of a COSM and a baseplates for polyoxime formation and choose an appropriate pH for a specific oximation reaction, taking into account pH stability of the molecules during the period of the oximation reaction.

The complementary orthogonal chemically reactive groups present on the baseplate structure are useful for chemoselectively ligating a COSM to the baseplate structure to create a polyoxime. For example, where the baseplate structure contains AOA groups and the COSM contains an aldehyde group such as glyoxylyl (GXL), parallel assembly due to chemoselective ligation of the complementary orthogonal chemical groups results rapidly and essentially quantitatively in the formation of a homogenous preparation of a polyoxime of defined structure.

In a further embodiment a baseplate can have at least one baseplate terminal residue attached to a reporter group or linker group, typically via a non-oxime linkage. The linker or reporter group can be ligated chemoselectively to the baseplate terminus or alternatively added during baseplate synthesis. A polyoxime containing an orthogonal linker group can be linked to a second polyoxime containing its complementary orthogonal linking group to yield a polyoxime dimer. Except for the complementarity of the linking groups, the polyoximes may be the same or different.

An individual COSMs is an organic molecule (which can contain an inorganic constituent) such as a peptide, a polypeptide, a lipid, an oligosaccharide, a nucleic acid sequence, or a combination of these molecular structures. Appropriately end-modified carborods are suitable COSMs. In an embodiment of the invention oxime formation occurs via aldehyde groups terminal to reducing sugars or created on sugars by mild chemical or enzymic oxidation. In another embodiment oxime formation occurs via an aldehyde group created by terminal oxidation of nucleic acid, such as exemplified by Reines and Cantor (Nucleic Acids Res. (1974) 1:767–786) for RNA, which is incorporated herein by reference, or created during chemical or enzymatic synthesis of a nucleic acid sequence. Such aldehydes are suitable complementary reactive groups to form oximes.

In one embodiment of this invention, a COSM is a peptide. In another embodiment, a COSM, and thus the polyoxime itself, is antigenic, preferably immunogenic. In another embodiment of this invention, a polyoxime with an haptenic or antigenic peptide COSM provides an antigenic molecule having increased valency, compared to the peptide alone, and increased immunogenicity. In vitro, antigenic polyoximes are useful as reagents for immunoassays to detect the presence of a protein. In vivo, antigenic polyoximes serve as immunogens useful as vaccines, for example. Polyvalency generally leads to higher binding and to higher specificity of interaction since more contacts are involved. In the case of a polyoxime comprising multiple copies of a ligand to a receptor, proximal receptors can be bridged if the COSM spacing and orientation provided by the baseplate is appropriate.

In view of the present disclosure, one skilled in the art can obtain a COSM having the appropriate complementary chemically reactive group. For example, a specifically active molecule such as a purified peptide COSM can be synthesized by SPPS. Following or during synthesis of the peptide, one of a pair of oxime-forming complementary orthogonal chemically reactive groups can be attached to the peptide using the methods described for the synthesis of baseplate structures. Other well-known methods also may be used to prepare polypeptide aldehydes, such as automated synthesis of peptide C-terminus aldehydes (see, for example, Murphy et al., *J. Amer. Chem. Soc.*, (1992) 114:3156–3157, which is incorporated herein by reference).

A COSM is further defined as consisting in part of a specifically active molecule or portion thereof. As used herein, the term "specifically active" indicates that the COSM has a defined biological, chemical or physical activity apart from its complementary orthogonal chemical reactivity. For example, a COSM may be specifically active as an antigen, an epitope or a hapten. Alternatively, a COSM may be specifically active as a receptor, such as a complementarily determining region of an antibody, or a ligand to a cell surface receptor.

As described herein for peptide baseplate structures, methods for regio-specific attachment or modification of C-termini via enzyme catalyzed reverse proteolysis or N-terminal serine or threonine residues (naturally present or engineered into the COSM) are applicable for COSM preparation. Natural or synthetic polypeptides carrying site-specifically placed aldehyde or amino-oxy groups also can be used as described, for example, by Offord, R. E., in *Protein Engineering: A Practical Approach*, pages 235–251, ed. Rees, et al. (Oxford Press, 1992), which is incorporated herein by reference. Reactive groups such as aldehydes can be placed site-specifically at the N-terminal of a recombinantly derived polypeptide (see for example Geoghegan et al. (Bioconjugate Chem. (1992) 3:138–146); Gaertner et al. (Bioconjugate Chem. (1992) 3:262–268). The combination of protein engineering by recombinant methods followed by site-specific modification to create COSMs capable of forming oxime linkages is a powerful tool for designing and creating homogeneous preparations of polyoximes of desired defined structure and activity. There is no limit on the size of the COSMs, as one merely prepares a baseplate in which the reactive groups are spaced further apart than in the present examples in order to accommodate larger polypeptide COSMs. Methods known in the art and as discussed herein for baseplate conformational design are applicable to COSM design as well.

A COSM also can be a specifically active chelator of metal ions or a molecule useful for binding a detectable marker. Such detectable markers include radionuclides, biotin, luciferin or a substrate for an enzymatic method of detection, such as 5-bromo-4-chloro-3-indolyl phosphate/ nitro blue tetrazolium, which is a substrate for alkaline phosphatase (Sambrook et al., *Molecular Cloning: A Laboratory Manual* 2d ed. (Cold Spring Harbor Laboratory Press 1989), which is incorporated herein by reference). Suitable metal chelating molecules include, but are not limited to, chelates of EDTA (ethylenediamine-tetraacetic acid) and analogs of EDTA as described in U.S. Pat. No. 4,678,667, which is incorporated herein by reference. Such analogs are capable of complexing with metal ions including radioactive metal ions as described in U.S. Pat. No. 4,622,420, which is incorporated by reference herein. COSMs may also consist of other chelators such as AOA-desferrioxamine, which chelates, for example, gallium-67 and gallium-68, or AOA-biocytin, which contains biotin in soluble form.

Where the metal ion is radioactive, such polyoximes are particularly useful in vivo for imaging or treating malignant tissues or a tumor. Using the present disclosure and available public knowledge, one of skill in the art would know how to construct baseplates containing these COSMs for in vitro diagnosis and in vivo diagnosis and treatment. For a description of general methodology, see, for example, U.S. Pat. Nos. 5,185,143, 5,011,676, 5,087,616, 4,707,352, 5,084,266, 4,918,164, 4,865,835, 4,861,581, 4,659,839, 4,652,440, and 4,444,744, which are incorporated herein by reference.

As noted above, parallel assembly of polyoximes by chemoselective ligation is the result of the complementary orthogonal chemical reaction between, for example, a GXL group on the baseplate structure and an AOA group on the COSM to form a homogeneous preparation of a polyoxime having a defined macromolecular structure. Other embodiments of polyoximes have the reverse complementary structures, i.e. amino-oxy baseplate and aldehydic second organic molecule, from those described above. These are particularly indicated when a series of aldehyde-containing molecules is available (e.g. sugars). However, generally preferred embodiments contain aldehyde baseplates.

The invention also provides methods of parallel assembly to create polyoximes. As described above, chemoselective ligation results in the formation of a homogeneous composition of polyoxime molecules having defined structure and characteristics. Example III demonstrates unexpected and surprising features of polyoxime formation by parallel assembly with baseplates of valency greater than two, including ease, rapidity, and mildness of synthesis; essentially quantitative yield; and apparent lack of steric hindrance.

Other functional groups including, but not limited to a reporter group (such as biotin or a chelator for a radiometal), a lipophilic anchor (such as tripalmitoyl-S-glycerol-Cys) or an orthogonal reactive linking group (such as bromoacetyl or a masked thiol such as S-acetylthioacetyl) can be added to the baseplate prior to oximation. Baseplates containing biocytin or N-acetyl-cysteine are provided in examples by way of illustration. The modified baseplates allow additional flexibility in using the polyoximes, such as for vaccines or biosensors. Reporter-tagged embodiments of polyoximes of the invention are monitored via the reporter group. Stable polyoximes possessing both a lipophilic anchor and a defined molecular structure are useful, for example, for insertion of the polyoxime into membranes, which can enhance vaccine production, or into other lipophilic environments. Attachment of the polyoximes to other macromolecules, to each other, or to surfaces is furthered by embodiments having a different non-oxime orthogonal reactive linking group for use in forming the desired linkage.

The di- and trivalent baseplates described in the following Examples section preserve symmetry. However, polyoximes with positional isomers can be formed, for example by using as a baseplate H-Gly$_3$-Lys(COCHO)-Lys(COCHO)-Gly-OH (SEQ ID NO:11); in such cases the environment of the first lysine is not identical to that of the second one. More generally, the baseplate can be deliberately synthesized to favor interaction with a target structure and have no symmetry.

In a separate embodiment, the polyoxime is further characterized as having the ability to induce an immune response in an animal. Immunogenic polyoximes that are formed from a baseplate structure covalently bonded to a plurality of a COSM with immunogenic properties have the ability to induce an immune response in the animal. For the purposes of illustration only, such a COSM can be a peptide or a polypeptide corresponding to a hapten, a cell surface receptor or fragment thereof, a metal chelating agent or the epitope of a viral antigen. Many different immunomodulating peptide COSMs exist, such as the peptides described by Hobbs et al. (*J. Immunol.* 138:2581–2586 (1987)), Antoni et al. (*J. Immunol.* 137:3201–3204 (1986)) and Nencioni et al. (*J. Immunol* 139: 800–804 (1987)), which are incorporated herein by reference. Various chelating agents also are well known and include, for example, the melanocyte stimulating hormone peptide derivatives (Eur. Pat. Appl. 0 498 771 A2, filed Mar. 2, 1992, which is incorporated herein by reference). These immunogenic polyoximes are useful in vivo as vaccines and imaging agents.

In another embodiment, COSMs can be nucleic acid sequences, which can be chemoselectively ligated to a baseplate. Nucleic acid sequences also can be coupled to peptide or polypeptide sequences to create a polypeptide-nucleic acid (PNA), which can be used as a COSM and ligated to a baseplate. When used in conjunction with detectable markers, such as $^{32}$P, biotin, radiolabelled chelators, or enzymes such as alkaline phosphatase (or a substrate thereof), the resulting polyoximes provide highly specific and reactive nucleic acid probes which are useful in various diagnostic techniques, for example, northern and Southern hybridization assays (see Sambrook et al. (1989)).

In a separate embodiment, the polyoxime has a plurality of a COSM which is a polypeptide having a sequence identical to the sequence of a complementarity determining region (CDR) of an antibody. As is known to one of skill in the art, the CDR may be coupled to a metal chelating agent to create a bifunctional COSM, or alternatively, the chelating or reporter agent is coupled to the baseplate as described herein. CDR polyoximes are useful in vitro and in vivo. In vitro, they can used in a place of polyclonal and monoclonal antibodies in various immunoassays. In vivo, they are useful to passively immunize an animal or to diagnose and treat a disease.

Polyoximes of the present invention are also useful in purifying biologically active molecules of interest that can bind to a polyoxime (for general methodology see for example Sambrook et al. (1989) and Harlow and Lane (1988)).

Polyoximes can be attached to a solid phase, such as the surface of a silicon chip, a tissue culture plate, or a synthetic or natural resin. One can chemoselectively ligate a polyoxime to a solid phase through the use, for example, of thiol groups temporarily protected with thiopyridyl or acetyl groups to form a thioether or a thioester bond. Alternatively, polyoximes can be attached to a solid phase, such as a lipid layer or cell membrane, via lipid anchor groups covalently attached to the baseplate portion of a polyoxime.

A soluble complex for targeting a biologically active module to a cell also is provided by this invention. The soluble complex is comprised of a baseplate structure ligated to a plurality of a biologically active molecule and linked to a cell specific binding agent. Alternatively, the baseplate can be ligated to a plurality of a cell specific binding agent and linked to a biologically active molecule. Such soluble complexes provide cell or tissue specific delivery systems to the cell expressing the appropriate receptor. Biologically active molecules include, but are not limited to, homogeneous antibody CDR, antibody fragments, epitopes, paratopes, nucleic acids, ligands specifically reactive with cellular receptors, and cellular receptors or fragments thereof that retain the ability to specifically bind their target molecule. The biologically active molecule also can be a peptide having attached thereto a therapeutic agent, for example, a toxin, chemotherapeutic agent or radioisotope. For the purposes of this invention, a cell specific binding agent is a molecule that recognizes and binds specific biological molecules. Such agents include but are not limited to antibodies, antibody fragments, and cell surface receptors (or biologically active fragments thereof). For example, the cell specific binding agent can be a tumor cell-specific receptor, a cell surface receptor, or a ligand for a cell surface receptor.

In addition to compositions containing only polyoximes, also within the scope of this invention are compositions containing polyoximes of the invention and at least one other ingredient. Also embodied are pharmaceutical compositions comprising a therapeutic polyoxime embodiment of the invention and a pharmaceutically acceptable carrier.

Also provided by this invention is a method of inducing an immune response in an animal which comprises administering to the animal an immunogenically effective amount of an antigenic polyoxime, defined above, in a pharmaceutically acceptable carrier. For the purposes of this invention, an animal is preferably a vertebrate, such as a mammal, especially a murine, simian or human. In one embodiment, the animal is a human patient. Depending on the antigenic polyoxime, the immune response that is induced is humoral or cellular immunity.

The polyoximes of the invention have several novel characteristics. One novel characteristic for synthetic molecules of this invention is that the polyoximes preparations are homogeneous. Polyoximes also are multivalent, are stable in aqueous solution or semi-aqueous solution, and can be prepared at temperatures from −3° C. to 50° C., but most advantageously at room temperature. The polyoximes of this invention have utilities related to the specific biological reactivity and specific chemical and physical reactivities of their individual component parts.

As demonstrated herein, the complementary reactive groups that interact to form an oxime linkage between baseplate and COSM are highly specific. The oximation reactions taught herein provided complete or essentially quantitative yield of the reaction product. Such complex molecule formation occurs under very mild conditions. Rapidity is particularly surprising under dilute conditions which are often useful to minimize inter-molecular aggregation or reactions. The oximation reaction can occur unattended, such that self-assembly of the polyoximes takes place. Polyoximes are easily purified by virtue of the essentially quantitative yield and because trace intermediates and the final product typically differ as molecules in a homologous series so that methods for their separation are readily chosen and applied. Oxime linkages have superior hydrolytic stability over a range of physiological conditions compared to hydrazones or the like. Oxime linkages are not commonly subject to enzymatic hydrolysis. Thus polyoximes have the advantage of being particularly suited to applications where integrity and stability of a complex is desirable. As demonstrated in the examples, the polyoximation reaction is very mild and thus is suitably advantageous for preparing biological macromolecules retaining biological activity or function. The polyoxime chemistry dispenses with the need to have reversible chemical protection of subunits. A great flexibility is provided herein for site-specific modification of both baseplates and COSMs to create reactive groups capable of forming oxime linkages. Because of this flexibility and the absence of the need for reversible protection, the design of baseplates and COSMs extends to both artificial and natural molecules and their derivatives. The surprising lack of steric hindrance demonstrated herein (e.g. a 23-mer peptide attached to each of the side-chains of seven consecutive lysine residues) indicates that complex molecules can now be designed. In such complex molecules the individual capabilities of the subunits can be enhanced and combined, the whole being greater than the sum of the parts. For example, baseplates can be designed to improve solubility of peptides as well as present peptides to receptors or antibodies or the immune system of an animal in multi-valent and/or constrained forms. Polyoximes formed from synthetic baseplates and COSMs have the additional advantage of being virus free.

The following examples are provided by way of illustration and not by way of limitation of aspects of the present invention.

EXAMPLE I

Synthesis of Peptide Baseplate Structures Having Chemically Reactive Aldehyde or Amino-Oxyacetyl Groups Synthesis of GXL-baseplate structures Peptide baseplate structures were constructed using solid phase peptide synthesis (SPPS). Briefly, automated SPPS was performed using a model 430A peptide synthesizer (Applied Biosystems, Inc.). The desired amino acid sequence was programmed into the synthesizer and synthesis proceeded using the standard Fmoc protocol. The starting resin was Gly-PAM polystyrene (0.5 mmol per synthesis). Two different peptide sequences were synthesized: H-Gly$_3$-[Lys(Boc)]$_5$-Gly-PAM (SEQ ID NO:13) resin and H-Gly$_3$-[Lys(Boc)]$_7$-Gly-PAM (SEQ ID NO:14) resin.

The Boc groups were removed using trifluoroacetic acid (TFA). Briefly, about 15 ml of TFA as incubated with one gram of resin for one hour at room temperature. The sample was then filtered, washed with dichloromethane and dried. The free α- and ε-amino groups were acylated using two equivalents of active Boc-Ser (benzyl) N-hydroxysuccinimide ester (0.16 M in dry DMSO) over each amino group. The apparent pH was measured using water-moistened pH paper and was adjusted to pH 8–9 with N-methylmorpholine. The resin was the agitated for two hours.

Following this reaction, the standard ninhydrin test showed that acylation was incomplete. Thus, the resin was filtered and the acylation reaction was repeated, maintaining the apparent pH 8–9 with N-methylmorpholine. Following this reaction, the ninhydrin test showed that acylation was essentially complete. The resin was filtered, washed with DMSO, then with dichloromethane and dried under vacuum. The reaction yielded 1.7 g resin from 1.3 g H-Gly$_3$-[Lys (Boc)]$_5$-Gly-PAM (SEQ ID NO:13) resin.

Cleavage-deprotection was achieved by dissolving the sample in 17 ml TFA. The mixture was stirred for 30 min, then 1.7 ml trifluoromethane sulfonic acid (TFMSA) was added. The solution was agitated for one hour and peptide was precipitated using dry ether. The peptide was washed three times with dry ether and dried under vacuum.

The resulting mixture of peptide and cleaved resin was resuspended in 60 ml water. The peptide, which is soluble in the water, was dissolved and the solution was filtered. Following lyophilization, the filtrate was dissolved in 50 ml water and purified in 5 ml portions by RP-HPLC (Waters) on a 250×21 mm id Nucleosil 300A 5 µm C8 column run at 10 ml/min. Solvent A was 0.1% TFA and solvent B was 0.1% TFA in 90% acetonitrile.

The peptide was purified isocratically at 100% A and eluted soon after the front. The column was then washed with 50% B and equilibrated with 100% A prior to the next injection. The product, H-Ser Gly$_3$-[Lys(H-Ser)]$_5$-Gly-OH (yield (SEQ ID NO:7)=100 mg) eluted as a single peak by analytical RP-HPLC (250×4 mm id column; packing and solvents as above) at 0.6 ml/min isocratic 100% A for 5 min, followed by a linear gradient of 2% per min B to 100% B. The retention time of the peptide was 20 min.

The purified peptide was characterized by electrospray ionization mass spectrometry (ESI-MS). A Trio 2000 spectrometer fitted with a 3000 amu rf generator was used (Fisons Instruments; Altrincham, UK). Samples were infused at 2 µl/min in water/methanol/acetic acid (49.5/49.5/1 by vol). The measured molecular weight of the sample was determined as 1410.12+/−0.66 daltons compared to the calculated expected value of 1409.56 daltons.

The serine groups on the precursor baseplate structure were converted into chemically reactive glyoxylyl (GXL) groups by mixing 0.2 ml H-Ser Gly$_3$-[Lys(H-Ser)]$_5$-Gly-OH (SEQ ID NO:7) (10 mM in water) with 7.8 ml imidazole-HCl buffer, pH 6.95, and adding 0.24 ml NaIO$_4$ (0.1 M in water). The mixture was rapidly mixed, then incubated at room temperature for 5 min. The oxidation reaction was terminated by adding 0.48 ml ethylene glycol (0.1 M in water) and rapid mixing the solution. The same was adjusted to pH 4.0 with acetic acid and the solution was injected onto a RP-HPLC 250×10 mm id Nucleosil 300A 7 µm C8 column. Elution was at 4 ml/min using isocratic 100% A for 5 min, followed by a linear gradient of 2% B/min to a final concentration of 100% B. The hexa-GXL-baseplate (SEQ ID NO:6) eluted at retention time of 16 min.

Solvent was removed by vacuum centrifugation (SpeedVac; Savant Instruments) without heating. The reaction yielded approximately 1 mg of purified hexa-GXL-baseplate, which was stored as a powder at −20° C. and was stable for at least several weeks. Similar methods were used to prepare octa-GXL-baseplate (SEQ ID NO:9).

Synthesis of AOA-Baseplate Structures

Alternatively, the ε-amino groups of the lysine residues in the baseplate peptide were converted to ε-AOA groups to create poly-AOA-baseplate structures. Briefly, H-Gly$_3$-Lys$_5$-Gly-PAM resin was incubated with Boc-AOA N-hydroxysuccinimide ester (0.1 M in dry DMSO; 2.5 equivalents over each amino group; 50 ml per 0.69 g resin, apparent pH 8–9 with N-methylmorpholine). The acylation reaction was complete after two hours incubation at room temperature, as shown by the standard ninhydrin test.

The resin was filtered, washed with DMSO, then dichloromethane and dried under vacuum. Cleavage-deprotection was achieved using a solution containing 7 ml TFA and 0.7 ml TFMSA. The sample was precipitated with ether, then dissolved in water, filtered and lyophilized as described above.

The lyophilized crude produce was dissolved in 4 ml water and 0.5 ml fraction were purified by RP-HPLC using the above-described 21 mm column operated at 10 ml/min. After 5 min elution at 100% A, a gradient of 1% B/min was applied to a final concentration of 5% B, which was maintained for 20 min. The column was washed with 50% B and equilibrated with 100% A prior to each injection.

The hexa-AOA-baseplate (SEQ ID NO:5) product eluted during the isocratic elution at 5% B. The product eluted as a single peak on analytical RP-HPLC. The mass was determined by ESI-MS to be 1325.49+/−0.38 daltons as compared to the calculated mass of 1325.4 daltons. Following removal of the solvent, the hexa-AOA-baseplate was stored as a powder at −20° C. and was stable for at least several weeks. The storage vial was kept tightly sealed and volatile aldehydes were excluded.

EXAMPLE II

Synthesis of Peptide Complementary Orthogonal Specifically Active Molecules (COSMs)

The peptide component of COSMs was synthesized using the SPPS method described above. A twelve amino acid peptide having the sequence KLEEQRPERVKG, which corresponds to amino acid residues 102 to 112 of human translationally controlled tumor protein (TCTP) containing an addition C-terminus glycine was synthesized. Automated peptide synthesis was performed using a model 430A peptide synthesizer (Applied Biosystems, Inc.) as described in Example I, except that a Sasrin resin (Bachem) was used and Pmc was used as side-chain protection for arginine residue.

The α-amino group of the lysine residue at the N-terminus of the TCTP peptide was converted to an α-AOA group by incubating 0.33 mmol TCTP-resin with Boc-AOA N-hydroxysuccinimide ester as described in Example I. Cleavage deprotection was performed using 1.5 ml of a mixture of phenol/ethanedithiol/thioanisole/water/TFA (0.75 g/0.25 ml/0.5 ml/0.5 ml/10 ml). Following stirring for three hours, the mixture was filtered and the peptide was precipitated with 4 ml cold methyl-tert-butyl ether. The precipitate was washed three times with the same ether and dried.

The dried precipitates were dissolved in 15 ml water and purified 1.5 ml portions by RP-HPLC on the 21 mm id column described in Example I. The column was eluted at 10 ml/min with 100% A for 5 min, then 1% B/min to a final concentration of 9% B, which was maintained until the product eluted (retention time approximately 45 min). The column was washed with 50% B and equilibrated with 100% A prior to each injection.

Following solvent removal by vacuum centrifugation, the AOA-TCTP (SEQ ID NO:4) sample was characterized by ESI-MS. The molecular weight of the sample was determined to be 1542.57+/−1.14 daltons, as compared to the expected value of 1541.73 daltons. The reaction yielded 120 mg AOA-TCTP from 1.3 g. AOA-polypeptidyl resin. The AOA-TCTP COSM was stored as a powder at −20° C. and was stable for at least several months.

Alternatively, an N-terminal serine residue was added to 707 mg (0.17 mmol) of the TCTP-Sasrin resin on the Applied Biosystems 430A peptide synthesizer. Following removal of the Fmoc group, cleavage-deprotection was performed as described for the AOA-TCTP COSM. The Ser-TCTP precursor COSM (SEQ ID NO:2) was purified by RP-HPCL (yield =90 mg) and characterized by ESI-MS. The molecular weight of the Ser-TCTP precursor COSM was determined to be 1556. 53+/−1.07 daltons as compared to the expected value of 1555.75 daltons. The Ser-TCTP precursor COSM was stored as a powder at −20° C. and is stable indefinitely.

The precursor was converted to the chemically reactive GXL-TCTP by adding 1.2 ml precursor Ser-TCTP COSM (10 mM in water) to a solution containing 6.8 ml imidazole-HCl buffer (50 mM, pH 6.95) and 0.24 ml NaIO$_4$ (0.1 M in water) and rapidly mixing the sample. After 5 min at room temperature, the oxidation reaction was stopped by addition of 0.48 ml ethylene glycol (0.1 M in water). The solution was adjusted to pH 4.0 with acetic acid and the GXL-TCTP was isolated by RP-HPLC on the 10 mm id column. Elution was performed at 4 ml/min with 100% A for 5 min followed by 2% B/min to 100% B. The retention time was 19 min.

After solvent removal, the GXL-TCTP was characterized by ESI-MS. The molecular mass of the sample was determined to be 1524.63+/−0.16 as compared to the expected value of 1524.70. The GXL-TCTP COSM was stored as a powder at −20° C. and was stable for at least several weeks.

A twenty-three amino acid peptide corresponding to residues 43 to 65 of the human proinsulin C peptide sequence (Pep C) also was synthesized on the Applied Biosystems 430A peptide synthesizer using the standard Fmoc protocol. Fmoc-Arg (Pmc)-Sasrin resin (Bachem) was used at a 0.5 mmol scale. While still protected as a resin-bound peptide, 100 mg resin (approximately 20 umol of the N-terminus α-amino group) was acylated using Boc-AOA N-hydroxysuccinimide ester as described above.

Following cleavage and deprotection using 3.5 ml of the phenol mixture described above, the AOA-Pep C COSM was purified by RP-HPLC (yield=8 mg). The molecular mass of the AOA-Pep C COSM was determined by ESI-MS to be 2308.56+/−0.11 daltons as compared to the calculated value of 2308.576 daltons. The AOA-Pep C COSM was stored as described above and was stable for at least several months.

EXAMPLE III

Parallel Assembly of Hexa-TCTP-Polyoximes by Chemoselective Ligation of a Hexa-GXL-Baseplate and AOA-TCTP COSMs Parallel assembly of the hexa-TCTP-polyoxime was initiated by adding 200 µl AOA-TCTP (SEQ ID NO:4) (10 mM in 0.1 M sodium acetate buffer, pH 4.6) to 6.7 µl hexa-GXL-baseplate structure (SEQ ID NO:6) (10 mM in water). After mixing, the oximation reaction was allowed to proceed at room temperature. AOA-TCTP (2 µmol) was present in about a five-fold molar excess over baseplate (67 nmol; about 400 nmol GXL groups). The structure of the predicted hexa-TCTP-polyoxime product is shown in FIG. 1.

Figure 2:
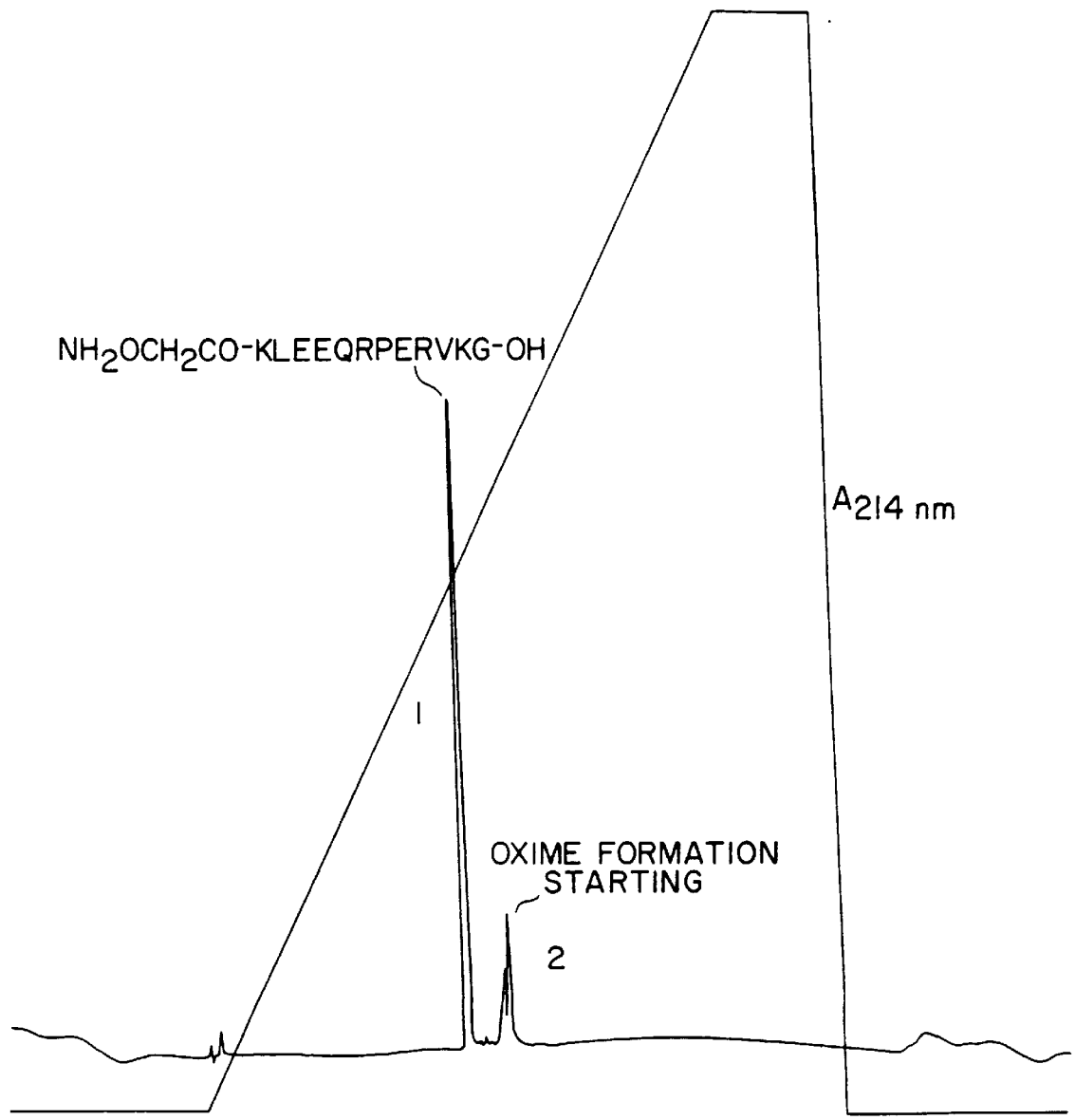
FIG. 2 shows the chromatogram obtained during RP-HPLC of a sample taken 3 hours after beginning the oximation reaction. Peak 1 indicates the fraction containing unbound TCTP-COSM, and Peak 2 indicates the fraction containing hexa-TCTP-polyoxime product.
Figure 3:
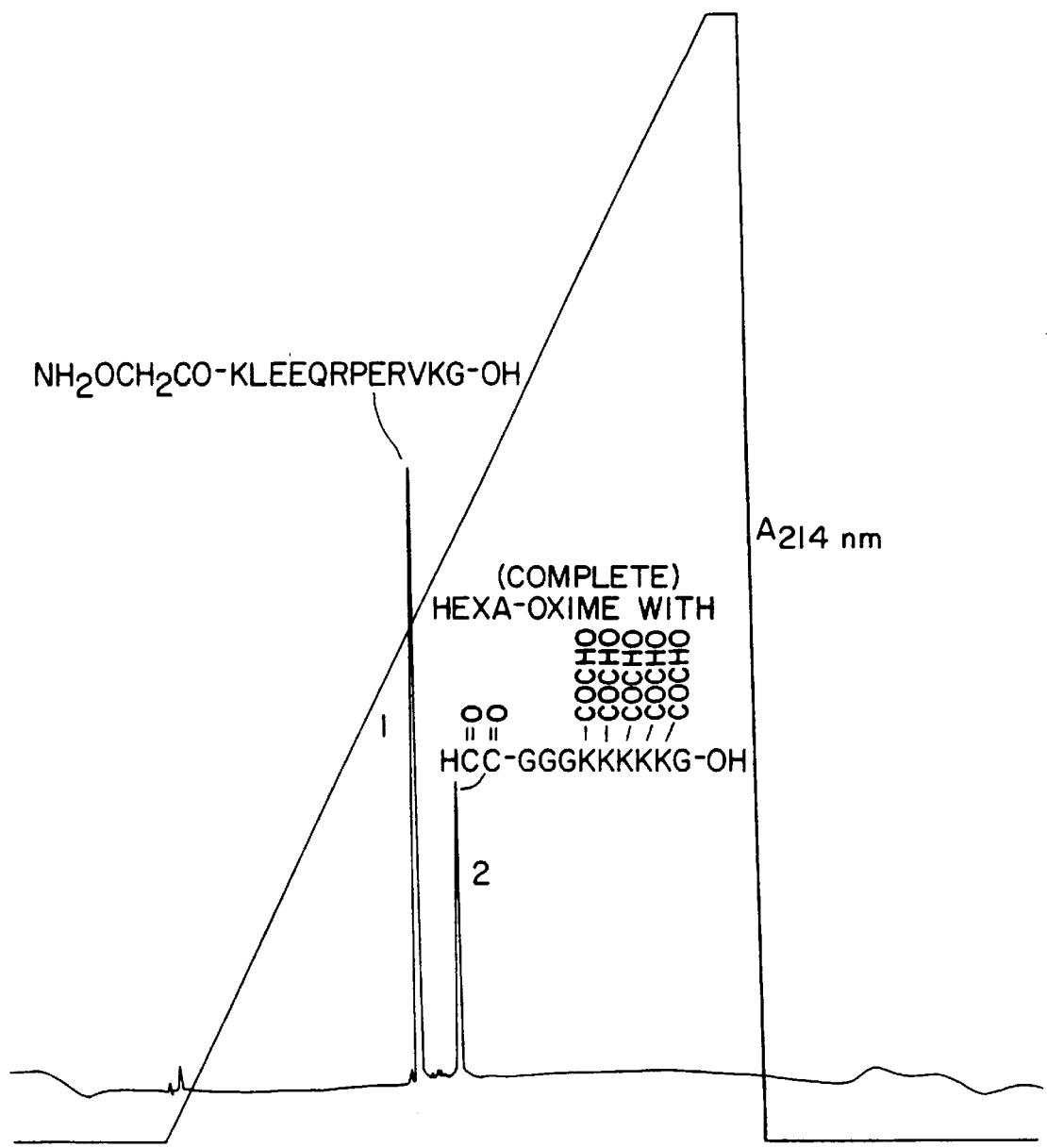
FIG. 3 shows the chromatogram obtained during RP-HPLC of a sample 18 hours after beginning the oximation reaction. Peak 1 indicates the fraction containing unbound TCTP-COSM, and Peak 2 indicates the fraction containing hexa-TCTP-polyoxime product.

The extent of chemoselective ligation was monitored by measuring the formation of the hexa-TCTP-polyoxime by RP-HPLC using the 4 mm id column. Elution was at 0.6 ml/min with 100% A for 5 min, followed by a gradient of 2% B/min from 0 to 100% B. Elution of the sample was monitored by absorption at 214 nanometers. Chromatograms obtained after 3 hours (FIG. 2) and after 18 hours of incubation (FIG. 3) are shown. After 3.5 hours of incubation the polyoxime peak, when analyzed on a shallower gradient, displayed a mixture of tri-, tetra-, penta- and hexa-oxime forms (data not shown). Formation of the hexa-TCTP-polyoxime was essentially complete after 18 hours of incubation.

The reaction was terminated and hexa-TCTP-polyoxime product was purified by preparative RP-HPLC. Reaction mixtures were purified in 0.5 ml portions on a 250×20 mm id column packed with Nucleosil 300A 5 µm C8. Elution was performed at 4 ml/min with 100% A for 5 min, followed by a linear gradient of 1% B/min to a final concentration of 100% B.

Excess AOA-TCTP eluted at a retention time of 44 min and hexa-TCTP-polyoxime product eluted at 50 min. Both the hexa-TCTP-polyoxime product and the excess of AOA-TCTP were recovered during purification. After vacuum desiccation, yield was calculated as 11 mg of hexa-TCTP-polyoxime obtained from 45 mg AOA-TCTP and 1.4 mg hexa-GXL-baseplate.

The hexa-TCTP-polyoxime was characterized by polyacrylamide gel electrophoresis in the presence of sodium dodecyl sulfate (SDS-PAGE) using the Phast system (Pharmacia). Protein samples were applied to a 20% gel and electrophoresis was performed at 15° C. for 90 volt-hours and visualized by silver stain. Protein molecular weight standards (Pharmacia) were run in parallel lanes and included phosphorylase-B (94 kDa), bovine serum albumin (67 kDa), ovalbumin (43 kDa), carbonic anhydrase (30 kDa), soybean trypsin inhibitor (20.1 kDa) and α-lactalbumin (14.4 kDa), as indicated in FIG. 4.

Figure 4:
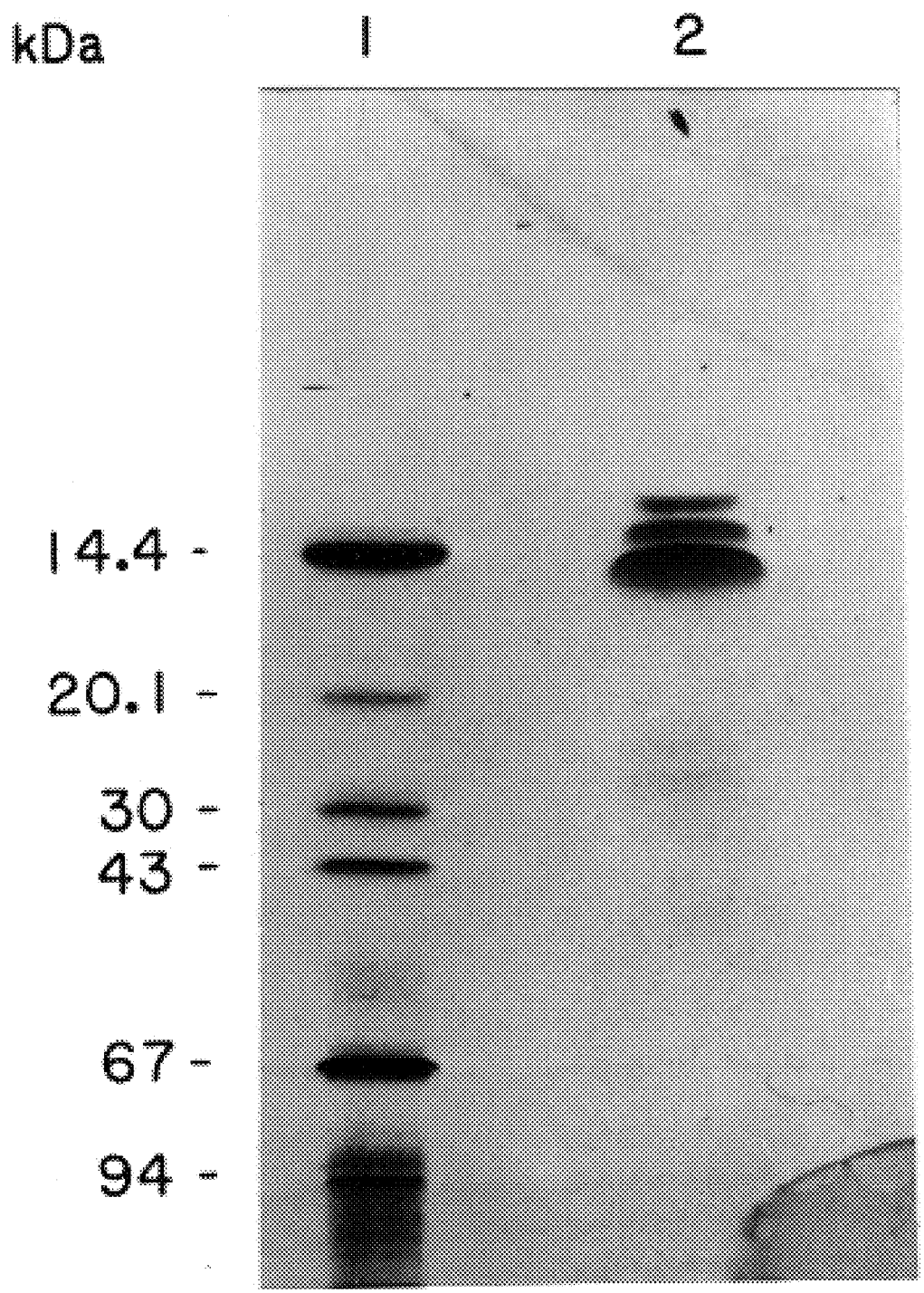
FIG. 4 is a photograph of a polyacrylamide gel showing the migration of the hexa-TCTP-polyoxime. Lane 1, protein standards. Lane 2, hexa-TCTP-polyoxime.

As shown in FIG. 4, the hexa-TCTP-polyoxime product migrated as a major band having an apparent molecular weight of about 14 kDa, which is greater than the predicted molecular weight of about 10 kilodaltons (kDa). The greater molecular weight is likely due to the expected extended structure of the hexa-TCTP-polyoxime. The presence of faint bands having faster mobility in the sample lane are likely due to partial decomposition of the same due to boiling the sample prior to gel loading. The stability of the hexa-TCTP-polyoxime is discussed below.

Figure 5:
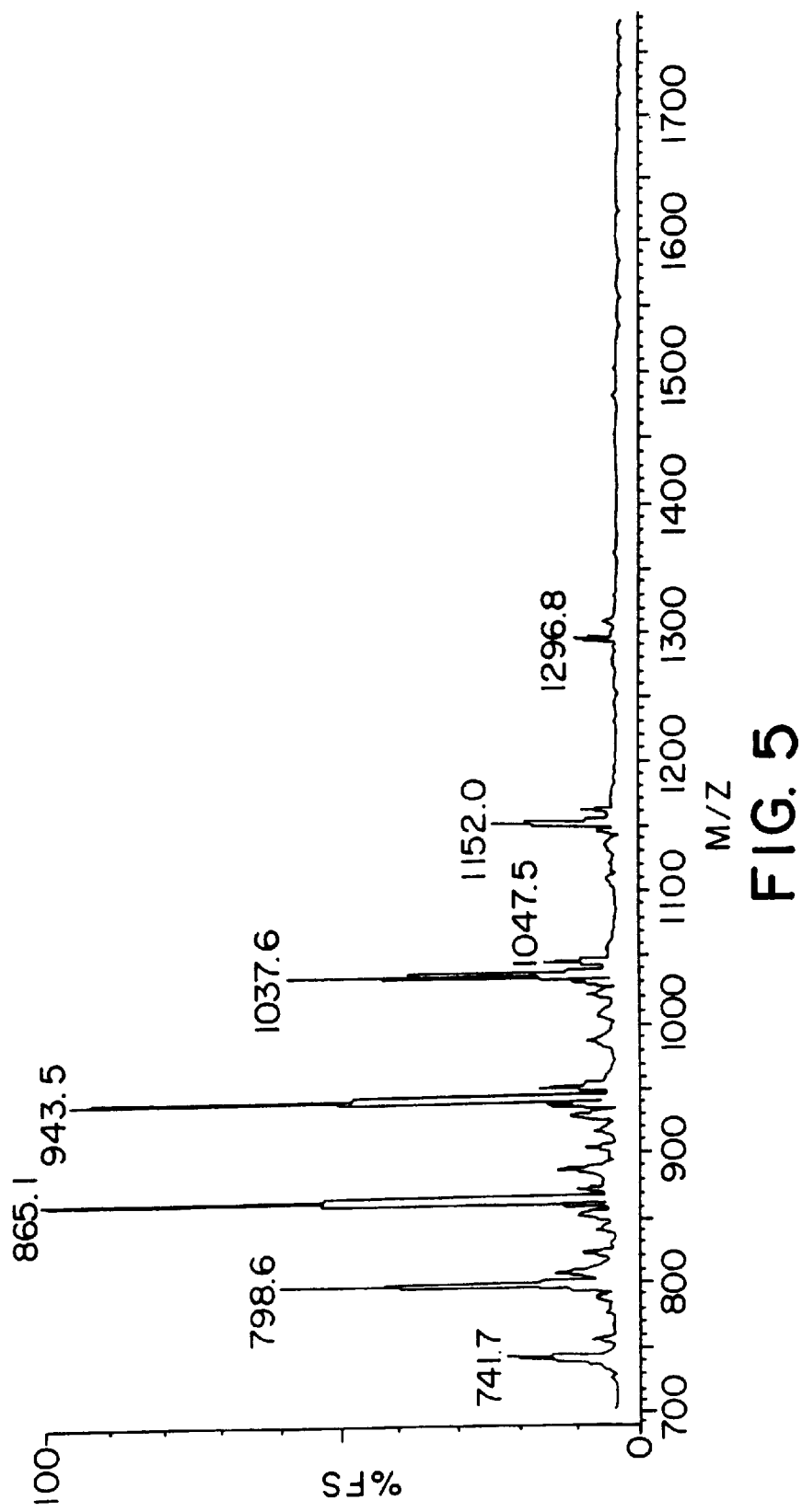
FIG. 5 shows a mass spectrum obtained by electrospray ionization mass spectrometry of the hexa-TCTP-polyoxime. Vertical axis indicates the percent full scale of detector response (% FS); horizontal axis indicates mass-to-charge ratio (M/Z). The numbers on the peaks indicate the M/Z value of each high molecular weight species that carries several positive charges (protons). For example, the peak at M/Z=1037.6 carries 10 protons (Z=10). The mass (M) of the corresponding species can be calculated as $(10)\times(1037.6)=10376$, minus 10 (for the ten protons) =10366 amu. The average mass calculated from all of the signals is 10367.41±1.28. The theoretical value is 10365.49.

The molecular weight was determined more precisely by electrospray ionization mass spectrometry. The molecular mass of the product was measured to be 10,367.41+/−1.28 daltons (FIG. 5), which compares favorably with the predicted molecular weight of 10,365.49 daltons expected for the chemoselective ligation of six TCTP COSMs (SEQ ID NO:4) to the hexa-GXL-baseplate structure (SEQ ID NO:6).

Figure 6:
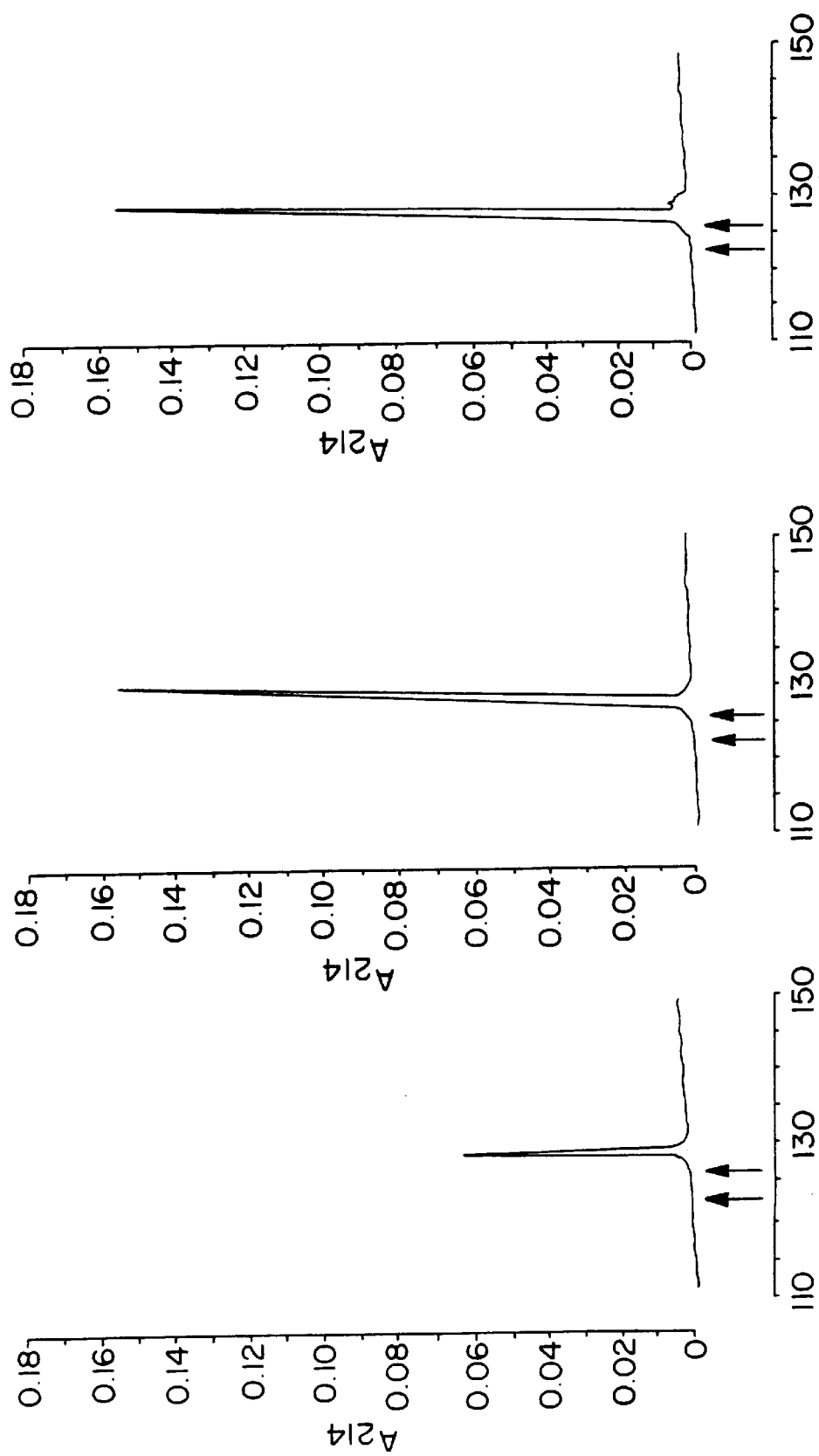
FIG. 6 shows chromatograms obtained during RP-HPLC of the hexa-TCTP-polyoxime following incubation for 48 hours at pH 2.1 (a), 24 hours at pH 4.6 (b) or 30.5 hours at pH 7.0 (c). Arrows indicate the expected elution times for incomplete penta-, tetra-, etc. TCTP-polyoximes; no partial products are observed.

The stability of the hexa-TCTP-polyoxime product was determined by incubating the hexaoxime (0.1 mg/ml) at room temperature for 48 hours in 0.1% TFA (pH 2.1), for 24 hours in 0.1 M sodium acetate (pH 4.6) or for 30.5 hours in phosphate buffered saline (pH 7.0). Following incubation, the samples were analyzed by RP-HPLC. As shown in FIG. 6, the hexa-TCTP-polyoxime was stable when incubated at the various pH values.

EXAMPLE IV

Parallel Assembly of Hexa-Pep C-Polyoximes by Chemoselective Ligation of a Hexa-GXL-Baseplate and AOA-Pep C COSMs Parallel assembly of the hexa-Pep C-polyoxime was initiated by adding 30 µl AOA-Pep C (10 mM in 01.M sodium acetate, pH 4.6) to 1 µl hexa-GXL-baseplate structure (10 mM in water) and incubating the mixture at room temperature. AOA-Pep C (SEQ ID NO:10) was present in a five-fold molar excess of AOA groups over each GXL group on the baseplate structure (SEQ ID NO:6). The structure of the expected hexa-Pep C-polyoxime is shown in FIG. 7.

Figure 8:
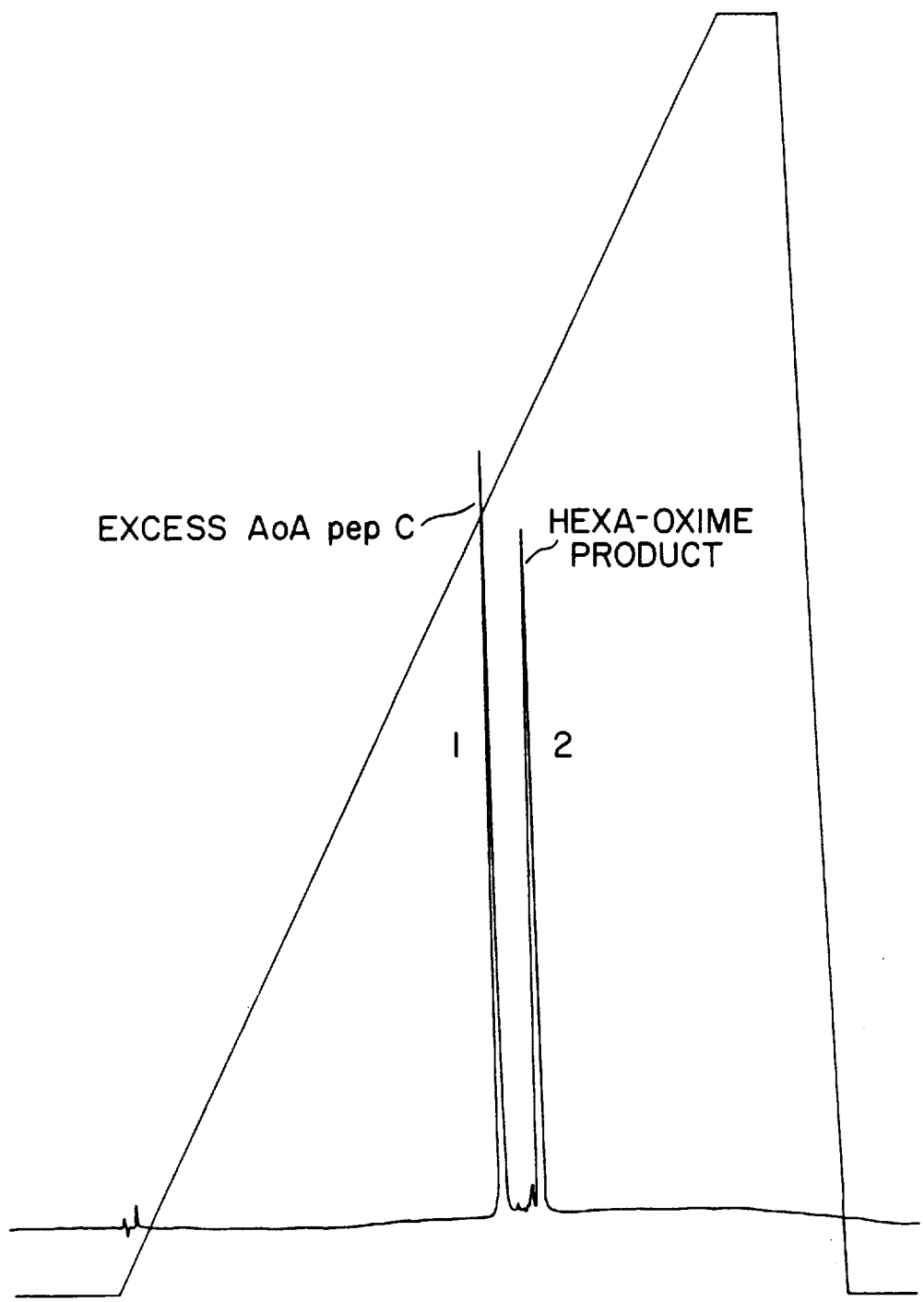
FIG. 8 shows the chromatogram obtained during RP-HPLC of sample taken 18 hours after beginning the oximation reaction. Peak 1 indicates the fraction containing unbound Pep C-COSM and Peak 2 indicates the fraction containing hexa-Pep C-polyoxime product.

The extent of chemoselective ligation was monitored by measuring the formation of the hexa-Pep C-polyoxime by RP-HPLC on the 4 mm id column. Elution was at 0.6 ml/min with 100% A for 5 min, followed by a gradient of 2% B/min to a final concentration of 100% B. FIG. 8 shows the chromatogram obtained after 18 hours of incubation. As was observed for the hexa-TCTP-polyoxime formation, hexa-Pep C-polyoxime formation was essentially complete after 18 hours of incubation. The reaction was terminated by performing preparative RP-HPLC, as described in Example III above.

Figure 9:
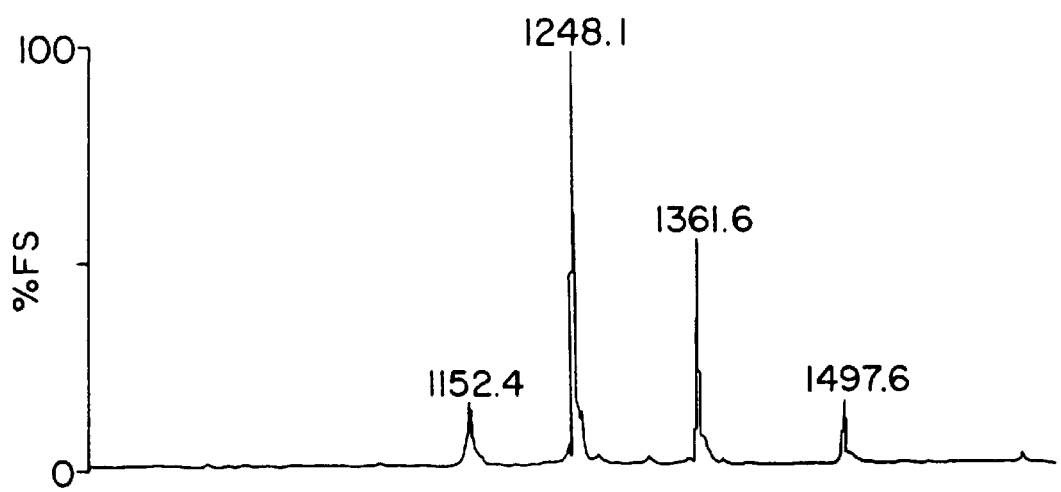
FIG. 9 shows a mass spectrum obtained by electrospray ionization mass spectrometry of the hexa-Pep C-polyoxime.
Figure 10:
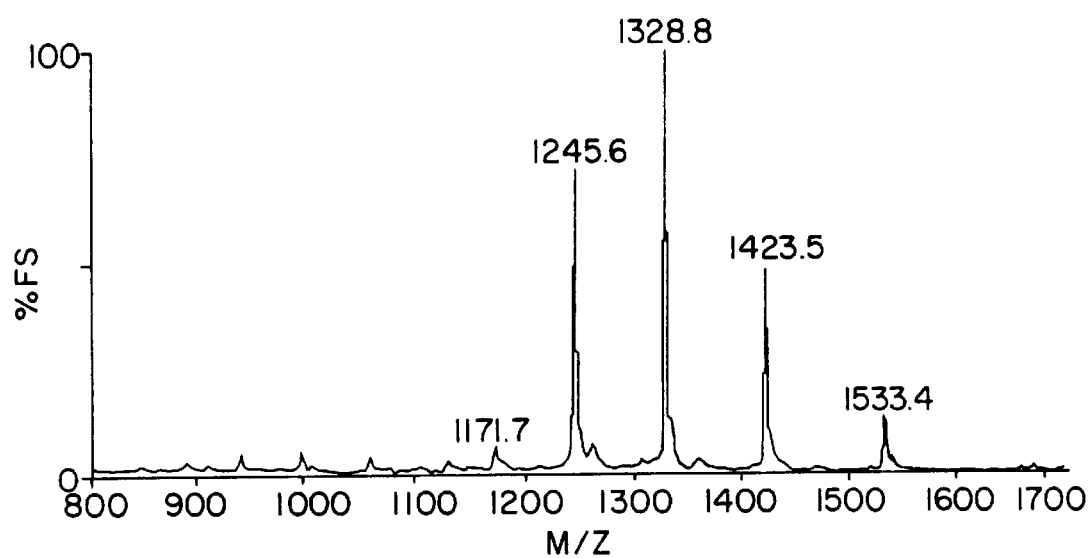
FIG. 10 shows a mass spectrum obtained by electrospray ionization mass spectrometry of an octa-Pep C-polyoxime.

Using electrospray ionization mass spectrometry, as described above, the molecular weight of the hexa-Pep C-polyoxime was measured to be 14,965.96+/−1.44 daltons as compared to be predicted value of 14,966.58 daltons for the ligation of six AOA-Pep C COSMs to the baseplate structure (FIG. 9). For comparison, an electrospray ionization mass spectrum is shown from an experiment in which AOA-Pep C COSMs (SEQ ID NO:10) were chemoselectively ligated to an octa-GXL-baseplate structure (SEQ ID NO:9) (FIG. 10). Again, the measured value of 19916.61+/− 3.05 daltons was comparable to the expected value of 19916.097 daltons for a polyoxime containing eight Pep C COSMs.

EXAMPLE V

Figure 11:
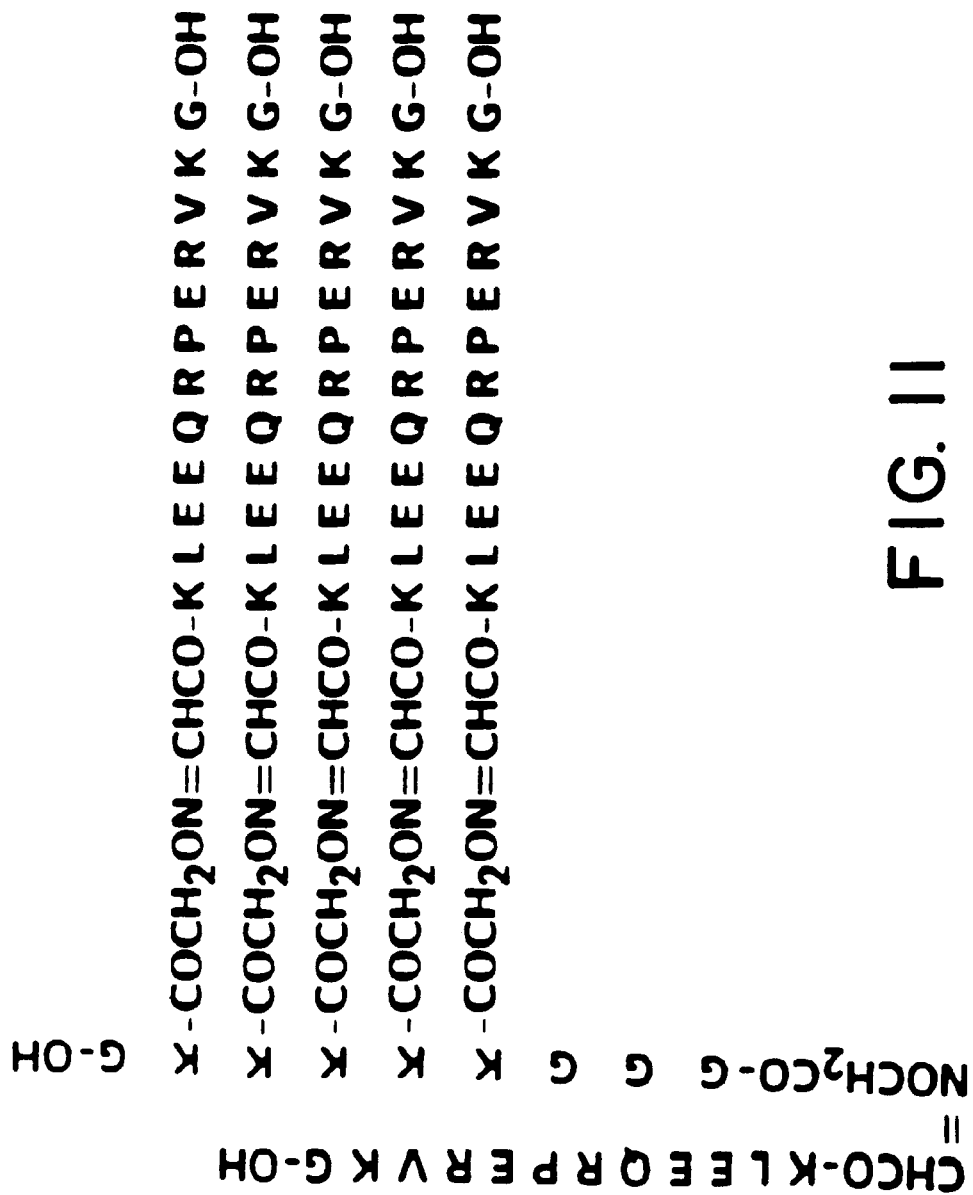
FIG. 11 depicts the structure of the hexa-TCTP-polyoxime. As indicated, a COSM is attached to each of the five ε-positions of the lysine residues in the baseplate structure and to the N-terminus of the baseplate structure. Note the stereochemistry of the oxime bonds as compared to the structure shown in FIG. 1.

Parallel Assembly of Hexa-TCTP-Polyoximes by Chemoselective Ligation of a Hexa-AOA-Baseplate and GXL-TCTP COSMs Parallel assembly of the hexa-TCTP-polyoxime was initiated by adding 1 µl hexa-AOA-baseplate structure (10 mM in water) to a mixture containing 180 µl 0.1 M sodium acetate buffer, pH 4.6, and 30 µl GXL-TCTP COSMs (10 mM in water). The sample was mixed and incubated at room temperature. GXL-TCTP (SEQ ID NO:3) was present in a five-fold molar excess over each AOA group on the baseplate (SEQ ID NO:5). The structure of the expected hexa-TCTP-polyoxime is shown in FIG. 11, which, except for the stereochemistry of the oxime bonds, is similar to the structure in FIG. 1.

The extent of chemoselective ligation was monitored by RP-HPLC, as described above, and formation of the hexa-TCTP-polyoxime was complete after 56 hours of incubation. No further change occurred during a 75 hour monitoring period. The reaction was terminated and hexa-TCTP-polyoxime product was purified by preparative RP-HPLC.

The molecular weight, as determined by electrospray ionization mass spectrometry, was measured to be 10,365.72 daltons as compared to the predicted molecular weight of 10,365.49 daltons expected for the ligation of six TCTP COSMs to the baseplate structure. The measured molecular weight also is very similar to the molecular weight of the product shown in FIG. 1, which was measured to be 10,367.41 daltons (see FIG. 5).

EXAMPLE VI

Preparation of a Smart Cluster using a COSM Having a C-terminal Aldehyde

The protease inhibitor, Leupeptin (Sigma Chem. Co), which contains a C-terminal aldehyde group, was chemoselectively ligated to a hexa-AOA-baseplate structure (SEQ ID NO:5). Thirty µl of Leupeptin (10 mM in water) and 180 µl sodium acetate buffer (0.1 M, pH 4.6) was added to 1 µl of hexa-AOA baseplate (10 mM in water). After incubating the reaction for 15 hours at room temperature, 20 µl of the reaction mixture wax removed and analyzed by RP-HPLC using the standard gradient of 2% B/min from 0% to 100% B, as described in Example I. The hexa-leupeptin-oxime eluted at a retention time 43 min. The mass of the hexa-leupeptin-oxime was measured by electrospray mass spectrometry to be 3776.45±0.70 daltons, which compares favorable with the expected value of 3775.66 daltons.

EXAMPLE VII

Immunization Using the Hexa-COSM-Polyoxime

About one hundred µg of the hexa-COSM-polyoxime, hexa-TCTP-polyoxime product shown in FIG. 1 in complete Freund's adjuvant was injected subcutaneously into about 10 sites in each of a group of rabbits. At intervals of about 4–6 weeks, rabbits were given booster injections containing 50 µg hexa-COSM-polyoxime in incomplete Freund's adjuvant. About 10–14 days after a booster injection, rabbits were bled and the blood serum was isolated. One skilled in the art would know that variations can be made in the amount of antigen used, the type of adjuvant, the site and method of injection and the timing of the injections (see, for example, Harlow and Lane (1988), chapter 5). Antiserum from hexa-TCTP-polyoxime immunized animals reacted with the antigen hexa-TCTP-polyoxime. The antiserum did not cross-react with TCTP proteins in an-immunoblot assay wherein TCTP protein was separated by two-dimensional SDS-PAGE and was probed with antiserum followed by labelled goat-anti-rabbit serum. Similarly, an octa-TCTP-MAP structure led to production of antibodies against the octa-TCTP-MAP (MAP is "Multiple Antigenic Peptide as disclosed by Tam et al. (1989)) which did not cross-react with TCTP protein, but in contrast to the hexa-TCTP-polyoxime gave an artifact by cross-reacting with the β-chain of haptoglobin in the immunoblot assay. Antibodies can be detected by using, for example, an immunodot blot assay and purified using methods well known in the art (see, for example, Harlow and Lane (1988), pages 178–179 and chapter 8).

EXAMPLE VIII

Preparation of a Polyoxime Having a Signal-producing Group

Signal-producing groups are attached to a COSM or to the baseplate structure either prior to or following the oximation reaction. An N-hydroxysuccinimide ester of biotin or Boc-biocytin N-hydroxysuccinimide ester is coupled to the α-amino group of H-Gly$_3$[Lys(Boc-Ser(benzyl)]$_5$-Gly-PAM resin using the standard conditions for peptide synthesis described above. Alternatively, a chelator group such as Fmoc-Lys (EDTA penta-t-butyl ester)-OH is coupled to a α-amino group of the baseplate structure using methods well known in the art (see, for example, Rana et al., Tetrahedron Lett. 33:4521–4524 (1992), which is incorporated herein by reference). Neither biotin nor EDTA is damaged by the cleavage-deprotection reaction, by the oxidation reaction to the GXL-baseplate or by the oximation reaction of the labeled baseplate structure with AOA-COSMs. The resulting poly-COSM-oxime contains a amino terminal biotin or EDTA group.

EXAMPLE IX

Attachment of Polyoximes to a Solid Surface

In order to attach a polyoxime to a solid surface chemoselective ligation can be used. For example, a polyoxime can be attached to a surface using thiol chemistry. Bromoacetyl-Gly$_3$-[Lys(Ser)]$_5$Gly-OH is made by standard solid phase peptide synthesis, oxidized to the penta-GXL-baseplate (SEQ ID NO:8), oximated with AOA-COSMs and purified by RP-HPLC, as described above.

Thiol groups are attached to surfaces using methods that are known in the art. A solid material containing aminopropyl groups on its surface is first acylated by treatment with S-acetylthioacetic acid N-hydroxysuccinimide ester. The acylated surface is then treated with dilute aqueous hydroxylamine to deacylate the surface and expose the reactive thiol groups. The bromoacetyl-polyoxime is coupled to the thiol groups on the solid surface by formation of a thioether bond under mild aqueous conditions at pH 4–9. Preferably, thioether formation is performed at pH 6.5–7.5 (see, for example, Brinkley, M., *Bioconj. Chem.* 3:2–13 (1992), which is incorporated herein by reference). Unbound material is removed by washing the surface.

EXAMPLE X

Cell-cell Attachment Mediated by Linked Polyoximes

Using methods discussed above a first polyoxime that contains COSM that recognizes and attaches to a tumor antigen is prepared a second polyoxime that contains COSM that recognizes and attaches to a cell surface receptor present, for example, on a macrophage, T cell or killer cell is prepared. The two polyoximes are constructed such that the C-termini or the N-termini of the baseplate structures have complementary orthogonal chemically reactive groups, such as a sulfhydryl group and bromoacetyl group.

The two polyoximes are then covalently linked by thioether formation under mild aqueous conditions at pH 4–9. Preferably, thioether formation is performed at pH 6.5–7.5. Following completion of the reaction, the bi-polyoximes are purified by standard methods such as gel filtration or RP-HPLC and are used to mediate cell attachment between cells containing the appropriate receptors or target molecules, such as a macrophage, T cell or killer cell and a tumor cell. Such bi-polyoximes are used to localize effector cells, such as those described above, to a target cell of interest, such as a tumor cell.

One skilled in the art would know that many different cell surface receptors and target molecules have been identified on different types of cells. Accordingly, the bi-polyoximes are constructed so as to mediate attachment of the particular cells of interest.

One skilled in the art would also recognize that bi-polyoximes can contain one type of COSM that recognizes and binds to a particular cell and a second type of COSM that is useful, for example, for binding a reporter molecule. Such bi-polyoximes are useful for detecting the presence and location of the particular cell in a heterogeneous population of cells or in an animal. Alternatively, the second type of COSM can bind an effector molecule, such as ricin, thereby directing the effector molecule to the particular cell of interest.

EXAMPLE XI

Parallel Assembly of Various Melanocyte Stimulating Hormone Analog-Polyoximes Synthetic polypeptide $NH_2OCH_2CO$-Nle-Asp-His-(D-Phe)-Arg-Trp-Lys-OH (an alpha-melanocyte stimulating hormone ("MSH") analog) carrying an N-terminal aminooxyacetyl group was prepared and separately incubated with a poly(aldehyde) baseplate molecule, e.g. terephthalaldehyde or OCH-CO-Gly$_3$-[Lys(COCHO)]$_5$-Gly-OH) (SEQ ID NO:6), in aqueous solution in acetate buffer, pH 4.6, at room temperature. The oximation reactions were followed by reversed phase HPLC as described. Reactions with di- and tri-valent aldehyde baseplates were rapid (1 h) while reactions with hexa-or octa-valent aldehyde baseplates took longer (about 16 h) but nevertheless proceeded close to completion. The final product was in each case characterized by mass spectrometry. All experimentally determined masses were in excellent agreement with the calculated values. Products were generally highly water-soluble, although this property will clearly depend on the hydrophilicity of the components used. Isomeric species were made by reversing the polarity of the oxime bond.

HPLC analysis showed polyoximes to be hydrolytically stable at room temperature at pH 2.1, 4.6 and 7.0 over at least 24 hours. Of course, these artificial proteins would be expected to be subject to deamidation, oxidation, microbial degradation, etc. as are natural polypeptides and proteins. As has been noted in work with hydrazones (e.g., King et al. Biochemistry 1986, 25:5774–5779; Kaneko et al. Bioconjugate Chem. 1991, 3:133–141), the hydrolytic stability of oximes is influenced by their structure, and our preliminary studies indicate that oxime stability increases in the series: $-CO-NH-CH_2-CH=N-O-CH_2<-NH-CO-CH=N-O-CH_2-<-C_6H_4-CH=N-O-CH_2-$. The stability of the oxime bond in vivo is sufficient to allow biodistribution studies of an immunoconjugate to be followed over several days in mice and also in the clinic.

EXAMPLE XII

Synthesis of a Divalent and a Trivalent Aldehyde Baseplate

Nitriloacetic acid (Fluka, 64 mg, 1 mmol carboxyl groups) was dissolved with sonication and slight warming in 15 ml DMF. 1 mmol N-hydroxy-succinimide solid (Fluka) was added and dissolved, then 1 ml of 1 M dicyclohexylcarbodiimide (Fluka) added. After overnight reaction at room temperature no DCC remained and the reaction was filtered to remove some DCC urea precipitate. To the filtrate was added 1.2 mmol aminoacetaldehyde diethylacetal (Fluka). After overnight reaction, 30 ml 0.1% trifluoroacetic acid was added followed by 1 ml 0.1% TFA in 90% acetonitrile and then 0.6 ml acetic acid. After thorough mixing, DCC urea was again removed by filtration through a Teflon membrane filter. The product was purified in 10 ml portions by preparative HPLC using the 250×20 mm column already described, monitored at 214 nm and run at 6 ml/min with the TFA system. After 5 min with solvent A (0.1% TFA), a linear gradient of 2% B/min was applied (B=0.1% TFA in 90% acetonitrile). The retention time of the trivalent acetal N[CH2—CO—NH—CH2—CH(OEt)2]$_3$ was 42 min and that of the divalent acetal N[CH2—CO—NH—CH2-CH (OEt)2]$_2$CH2—CO2H was 35 min. The products were identified by FAB-MS: m/z 537 for M+H$^+$ of the trivalent acetal and 422 for M+H$^+$ of the divalent acetal.

After removal of solvents on the rotary evaporator and by lyophilization, deacetalization was effected with 5% TFA at 37° C. for 2 h. The trialdehyde decomposed if the 5% TFA solution was directly evaporated, so instead product N[CH2—CO—NH—CH2—CHO]$_3$ was isolated by injecting small (30 µl) portions on the preparative column operated at 6 ml/min isocratically with solvent A, washing the column with 100% B between injections. The excess TFA from the deprotection eluted with retention time 11 min and the product tri-aldehyde baseplate eluted at 13 min. The tri-aldehyde solution was adjusted to pH about 3 with 1 M NaOH and stored at −20 C. The divalent aldehyde baseplate was similarly isolated.

EXAMPLE XIII

Preparation of Asymmetrical Divalent and Symmetrical Trivalent Polyoximes

Oximation between the trivalent symmetrical baseplate N[CH2—CO—NH—CH2—CHO]$_3$ and the amino-oxyacetyl-alpha-MSH analogue was carried out as previously described. The polyoxime eluted from analytical HPLC (250×4 mm id column, 0.6 ml/min, 2% B/min gradient) with retention time of 36 min.

NH$_2$OCH$_2$CO-Nle-Asp-His-(D-Phe)-Arg-Trp-Lys-OH reacted smoothly with a terephthalaldehyde to give the homodimer p-C$_6$H$_4$[CH=NOCH$_2$CO-Nle-Asp-His-(D-Phe)-Arg-Trp-Lys-OH]$_2$ characterized by ESI-MS (FIG. 12). It is known that the alpha-MSH analogue Nle-Asp-His-(D-Phe)-Arg-Trp-Lys binds to melanoma cells even when modified at the alpha-amino group and when linked as a homodimer through this group (Bagutti et al. (Prog. Histochem. Cytochem. (1992) 26:110–118). In the case of MSH, the biological activity can be measured, for example, with an in situ melanin assay in which the peptide is tested for stimulation of B16-F1 melanoma cells.

The present invention now provides the means to synthesize rapidly for screening polyoxime multimers of biological compounds, such as MSH, having varying spacing, charge, lipophilicity, valency, conformational restraints, solubility and other desirable physical and biological (e.g immunological) properties.

EXAMPLE XIV

Synthesis of an Acetyl-cysteine Baseplate

Fmoc-Cys(Trt)-OSu 0.2 mmol in 20 ml dry DMSO was added to 0.1 mmol H-Gly3-Lys[Boc-Ser(Bzl)-]5-Gly-OCH2-PAM- (SEQ ID NO:15) resin. After a few hours mixing at an apparent pH of 8 (adjusted with N-methyl morpholine), acylation was complete (ninhydrin test). Fmoc was removed as usual (DMF/piperidine) and the free amino group acetylated with 5 equivalents of acetic anhydride in DMF using N-methyl morpholine as base. The resin was treated in the conventional way (Applied Biosystems Inc. protocol, mixture C) with TFA, TFMSA and scavengers to deprotect and cleave. Product was purified by HPLC on a 250×4 mm id column operated at 0.6 ml/min with the TFA system, 1% B/min after an initial 5 min at 100% A. The product eluted as a major peak at retention time 25 min and was characterized by ESI-MS (found 1467.92+/−0.79; calc. 1466.62).

Although the invention has been described with reference to the above-provided embodiments, it should be understood that various modifications can be made without departing from the scope and spirit of the invention. Accordingly, the scope of the invention is limited only by the following claims.

This application is a companion application to U.S. application Ser. No. 08/105,904 (attorney docket no. ABIC-001/02 US), which was filed on even date with the present application and is herein incorporated by reference.

We claim:

1. A homogeneous polyoxime composition, in which polyoxime molecules present in said composition comprise a first organic baseplate molecule linked via a plurality of at least three oxime linkages to said plurality of second organic molecules, said oxime linkages being formed by reaction of an orthogonal reactive group on each said second organic molecule with a complementary orthogonal reactive group on said baseplate, wherein said orthogonal reactive group and said complementary orthogonal reactive group are selected from the group consisting of an aldehyde group, a keto group and an amino-oxy group, as appropriate for complementarity, wherein said second organic molecules are identical in structure, wherein said at least three complementary orthogonal reactive groups on said baseplate are identical groups and wherein said first organic baseplate molecule is other than a heterogeneous antibody glycoprotein preparation modified by chemical or enzymatic oxidation of sugar residues.

2. The composition of claim 1, wherein said baseplate is formed at least in part from amino acid residues.

3. The composition of claim 1, wherein said complementary orthogonal reactive group on said baseplate comprises an aldehyde group.

4. The composition of claim 1, wherein said complementary orthogonal reactive group on said baseplate comprises amino-oxy-acetyl.

5. The composition of claim 1, wherein said orthogonal reactive group in said second organic molecule comprises amino-oxy-acetyl.

6. The composition of claim 1, wherein said oxime linkage is selected from the group consisting of —CO—NH—CH$_2$—CH=N—O—CH$_2$, —NH—CO—CH=N—O—CH$_2$—, and —C$_6$H$_4$—CH=N—O—CH$_2$—.

7. The composition of claim 1, wherein said second organic molecule is selected from the group consisting of peptides, lipids, oligosaccharides, nucleic acids, and macromolecules formed by a combination thereof.

8. The composition of claim 1, wherein said polyoxime is immunogenic.

9. The composition of claim 1, wherein said second organic molecule comprises a polypeptide having a complementarity determining region of a native antibody.

10. The composition of claim 1, further comprising a third organic molecule linked to the baseplate and selected from the group consisting of metal chelating agents, detectable markers, lipophilic anchors, imaging agents, and therapeutic agents.

11. The composition of claim 1, wherein said second organic molecule comprises a member selected from the group consisting of metal chelating agents, detectable markers, lipophilic anchors, imaging agents, and therapeutic agents.

12. A pharmaceutical composition, comprising the polyoxime composition of claim 1 and a pharmaceutically acceptable carrier.

13. The pharmaceutical composition of claim 12, wherein said polyoxime composition is immunogenic and is present in an immunogenically effective amount.

14. A method of inducing an immune response in an animal, which comprises administering to said animal an immunologically effective amount of the composition of claim 13.

15. A method of imaging a cell, comprising selecting a polyoxime composition of claim 10 or 11 comprising an imaging agent and contacting the cell with a detectable amount of the polyoxime composition.

16. A homogeneous polyoxime composition prepared by a process comprising the steps of:
   1) obtaining a first organic baseplate molecule having present therein a plurality of at least three identical orthogonal reactive groups capable of oxime linkage formation, wherein said orthogonal reactive groups are amino-oxy groups, aldehyde groups or keto groups;
   2) obtaining a plurality of second organic molecules, each molecule having present therein a complementary orthogonal reactive group capable of oxime linkage formation with said orthogonal reactive group on said baseplate molecule, wherein said complementary orthogonal reactive groups are amino-oxy groups, aldehyde groups or keto groups, as appropriate for complementarity, and wherein said second organic molecules are identical in structure;

3) contacting said baseplate molecule with an amount of said second organic molecules sufficient for essentially complete reaction between said second organic molecules and said plurality of orthogonal reactive groups on said baseplate molecule under conditions allowing oxime linkage formation, whereby oxime linkage formation occurs between the orthogonal reactive groups on said baseplate and the complementary orthogonal reactive groups on said second organic molecules; and 4) separating the polyoxime product from unreacted second organic molecules.

17. A method of producing a homogeneous polyoxime composition, comprising the steps of:

1) obtaining a first organic baseplate molecule having present therein a plurality of at least three identical orthogonal reactive groups capable of oxime linkage formation, wherein said orthogonal reactive groups are amino-oxy groups, aldehyde groups or keto groups, and wherein said second organic molecules are identical in structure;

2) obtaining a plurality of second organic molecules each molecule having present therein a complementary orthogonal reactive group capable of oxime linkage formation with said orthogonal reactive group on said baseplate molecule, wherein said complementary orthogonal reactive groups are amino-oxy groups, aldehyde groups or keto groups, as appropriate for complementarity;

3) contacting said baseplate molecule with an amount of said second organic molecules sufficient for essentially complete reaction between said second organic molecules and said plurality of orthogonal reactive groups on said baseplate molecule under conditions allowing oxime linkage formation, whereby oxime linkage formation occurs between the orthogonal reactive groups on said baseplate and the complementary orthogonal reactive groups on said second organic molecules; and 4) separating the polyoxime product from unreacted second organic molecules.

18. The method of claim 17, wherein said contacting mixing occurs at a pH equal to or less than 5.

* * * * *

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
      (A) LENGTH: 12 amino acids
      (B) TYPE: amino acid
      (D) TOPOLOGY: linear (ii) MOLECULE TYPE: peptide (iii) HYPOTHETICAL: NO (xi) SEQUENCE DESCRIPTION: SEQ ID NO:1:

Lys Leu Glu Glu Gln Arg Pro Glu Arg Val Lys Gly
1               5                   10

(2) INFORMATION FOR SEQ ID NO:2:

(i) SEQUENCE CHARACTERISTICS:
      (A) LENGTH: 13 amino acids
      (B) TYPE: amino acid
      (D) TOPOLOGY: linear (ii) MOLECULE TYPE: peptide (iii) HYPOTHETICAL: NO (xi) SEQUENCE DESCRIPTION: SEQ ID NO:2:

Ser Lys Leu Glu Glu Gln Arg Pro Glu Arg Val Lys Gly
1               5                   10

```
(2) INFORMATION FOR SEQ ID NO:3:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (iii) HYPOTHETICAL: NO (ix) FEATURE:
         (A) NAME/KEY: Modified-site
         (B) LOCATION: 1
         (D) OTHER INFORMATION: Glyoxylyl-Lys (glyoxylyl hereinafter
             GXL)

(xi) SEQUENCE DESCRIPTION: SEQ ID NO:3:

Lys Leu Glu Glu Gln Arg Pro Glu Arg Val Lys Gly
1               5                   10

(2) INFORMATION FOR SEQ ID NO:4:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (ix) FEATURE:
         (A) NAME/KEY: Modified-site
         (B) LOCATION: 1
         (D) OTHER INFORMATION: Aminooxyacetyl-Lys (aminooxyacetyl
             hereinafter AOA)

(xi) SEQUENCE DESCRIPTION: SEQ ID NO:4:

Lys Leu Glu Glu Gln Arg Pro Glu Arg Val Lys Gly
1               5                   10

(2) INFORMATION FOR SEQ ID NO:5:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (iii) HYPOTHETICAL: NO (ix) FEATURE:
         (A) NAME/KEY: Modified-site
         (B) LOCATION: 1
         (D) OTHER INFORMATION: AOA-Gly (ix) FEATURE:
         (A) NAME/KEY: Modified-site
         (B) LOCATION: 4
         (D) OTHER INFORMATION: Lys-AOA (ix) FEATURE:
         (A) NAME/KEY: Modified-site
         (B) LOCATION: 5
         (D) OTHER INFORMATION: Lys-AOA (ix) FEATURE:
         (A) NAME/KEY: Modified-site
         (B) LOCATION: 6
         (D) OTHER INFORMATION: Lys-AOA (ix) FEATURE:
         (A) NAME/KEY: Modified-site
         (B) LOCATION: 7
         (D) OTHER INFORMATION: Lys-AOA
```

```
    (ix) FEATURE:
         (A) NAME/KEY: Modified-site
         (B) LOCATION: 8
         (D) OTHER INFORMATION: Lys-AOA (xi) SEQUENCE DESCRIPTION: SEQ ID NO:5:

Gly Gly Gly Lys Lys Lys Lys Lys Gly
1               5

(2) INFORMATION FOR SEQ ID NO:6:

(i) SEQUENCE CHARACTERISTICS:
         (A) LENGTH: 9 amino acids
         (B) TYPE: amino acid
         (D) TOPOLOGY: linear (ii) MOLECULE TYPE: peptide (iii) HYPOTHETICAL: NO (ix) FEATURE:
         (A) NAME/KEY: Modified-site
         (B) LOCATION: 1
         (D) OTHER INFORMATION: GXL-Gly (ix) FEATURE:
         (A) NAME/KEY: Modified-site
         (B) LOCATION: 4
         (D) OTHER INFORMATION: Lys-GXL (ix) FEATURE:
         (A) NAME/KEY: Modified-site
         (B) LOCATION: 5
         (D) OTHER INFORMATION: Lys-GXL (ix) FEATURE:
         (A) NAME/KEY: Modified-site
         (B) LOCATION: 6
         (D) OTHER INFORMATION: Lys-GXL (ix) FEATURE:
         (A) NAME/KEY: Modified-site
         (B) LOCATION: 7
         (D) OTHER INFORMATION: Lys-GXL (ix) FEATURE:
         (A) NAME/KEY: Modified-site
         (B) LOCATION: 8
         (D) OTHER INFORMATION: Lys-GXL (xi) SEQUENCE DESCRIPTION: SEQ ID NO:6:

Gly Gly Gly Lys Lys Lys Lys Lys Gly
1               5

(2) INFORMATION FOR SEQ ID NO:7:

(i) SEQUENCE CHARACTERISTICS:
         (A) LENGTH: 10 amino acids
         (B) TYPE: amino acid
         (D) TOPOLOGY: linear (ii) MOLECULE TYPE: peptide (iii) HYPOTHETICAL: NO (ix) FEATURE:
         (A) NAME/KEY: Modified-site
         (B) LOCATION: 5
         (D) OTHER INFORMATION: Lys-Serine (ix) FEATURE:
         (A) NAME/KEY: Modified-site
         (B) LOCATION: 6
         (D) OTHER INFORMATION: Lys-Serine
```

(ix) FEATURE:
            (A) NAME/KEY: Modified-site
            (B) LOCATION: 7
            (D) OTHER INFORMATION: Lys-Serine (ix) FEATURE:
            (A) NAME/KEY: Modified-site
            (B) LOCATION: 8
            (D) OTHER INFORMATION: Lys-Serine (ix) FEATURE:
            (A) NAME/KEY: Modified-site
            (B) LOCATION: 9
            (D) OTHER INFORMATION: Lys-Serine (xi) SEQUENCE DESCRIPTION: SEQ ID NO:7:

Ser Gly Gly Gly Lys Lys Lys Lys Lys Gly
1               5                   10

(2) INFORMATION FOR SEQ ID NO:8:

(i) SEQUENCE CHARACTERISTICS:
            (A) LENGTH: 9 amino acids
            (B) TYPE: amino acid
            (D) TOPOLOGY: linear (ii) MOLECULE TYPE: peptide (iii) HYPOTHETICAL: NO (ix) FEATURE:
            (A) NAME/KEY: Modified-site
            (B) LOCATION: 4
            (D) OTHER INFORMATION: Lys-GXL (ix) FEATURE:
            (A) NAME/KEY: Modified-site
            (B) LOCATION: 5
            (D) OTHER INFORMATION: Lys-GXL (ix) FEATURE:
            (A) NAME/KEY: Modified-site
            (B) LOCATION: 6
            (D) OTHER INFORMATION: Lys-GXL (ix) FEATURE:
            (A) NAME/KEY: Modified-site
            (B) LOCATION: 7
            (D) OTHER INFORMATION: Lys-GXL (ix) FEATURE:
            (A) NAME/KEY: Modified-site
            (B) LOCATION: 8
            (D) OTHER INFORMATION: Lys-GXL (xi) SEQUENCE DESCRIPTION: SEQ ID NO:8:

Gly Gly Gly Lys Lys Lys Lys Lys Gly
1               5                   10

(2) INFORMATION FOR SEQ ID NO:9:

(i) SEQUENCE CHARACTERISTICS:
            (A) LENGTH: 11 amino acids
            (B) TYPE: amino acid
            (D) TOPOLOGY: linear (ii) MOLECULE TYPE: peptide (iii) HYPOTHETICAL: NO (ix) FEATURE:
            (A) NAME/KEY: Modified-site
            (B) LOCATION: 1
            (D) OTHER INFORMATION: GLX-Gly (ix) FEATURE:
    (A) NAME/KEY: Modified-site
    (B) LOCATION: 4
    (D) OTHER INFORMATION: Lys-GLX (ix) FEATURE:
    (A) NAME/KEY: Modified-site
    (B) LOCATION: 5
    (D) OTHER INFORMATION: Lys-GLX (ix) FEATURE:
    (A) NAME/KEY: Modified-site
    (B) LOCATION: 6
    (D) OTHER INFORMATION: Lys-GLX (ix) FEATURE:
    (A) NAME/KEY: Modified-site
    (B) LOCATION: 7
    (D) OTHER INFORMATION: Lys-GLX (ix) FEATURE:
    (A) NAME/KEY: Modified-site
    (B) LOCATION: 8
    (D) OTHER INFORMATION: Lys-GLX (ix) FEATURE:
    (A) NAME/KEY: Modified-site
    (B) LOCATION: 9
    (D) OTHER INFORMATION: Lys-GLX (ix) FEATURE:
    (A) NAME/KEY: Modified-site
    (B) LOCATION: 10
    (D) OTHER INFORMATION: Lys-GLX (xi) SEQUENCE DESCRIPTION: SEQ ID NO:9:

```
Gly Gly Gly Lys Lys Lys Lys Lys Lys Gly
1               5                   10
```

(2) INFORMATION FOR SEQ ID NO:10:

(i) SEQUENCE CHARACTERISTICS:
        (A) LENGTH: 23 amino acids
        (B) TYPE: amino acid
        (D) TOPOLOGY: linear (ii) MOLECULE TYPE: peptide (iii) HYPOTHETICAL: NO (ix) FEATURE:
        (A) NAME/KEY: Modified-site
        (B) LOCATION: 1
        (D) OTHER INFORMATION: AOA-Glu (xi) SEQUENCE DESCRIPTION: SEQ ID NO:10:

```
Glu Leu Gly Gly Gly Pro Gly Ala Gly Ser Leu Gln Pro Leu Ala Leu
1               5                   10                  15

Glu Gly Ser Leu Gln Lys Arg
            20
```

(2) INFORMATION FOR SEQ ID NO:11:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (iii) HYPOTHETICAL: NO (ix) FEATURE:

(A) NAME/KEY: Modified-site
        (B) LOCATION: 4
        (D) OTHER INFORMATION: Lys-GXL (ix) FEATURE:
        (A) NAME/KEY: Modified-site
        (B) LOCATION: 5
        (D) OTHER INFORMATION: Lys-GXL (xi) SEQUENCE DESCRIPTION: SEQ ID NO:11:

Gly Gly Gly Lys Lys Gly
1               5

(2) INFORMATION FOR SEQ ID NO:12:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (iii) HYPOTHETICAL: NO (ix) FEATURE:
        (A) NAME/KEY: Modified-site
        (B) LOCATION: 1
        (D) OTHER INFORMATION: AOA-Tyr (xi) SEQUENCE DESCRIPTION: SEQ ID NO:12:

Tyr Arg Glu Asp Gly Val Thr Pro Tyr Met Ile Phe Phe Lys Asp Gly
1               5                   10                  15

Leu Glu Met Glu Lys
            20

(2) INFORMATION FOR SEQ ID NO:13:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (iii) HYPOTHETICAL: NO (ix) FEATURE:
        (A) NAME/KEY: Modified-site
        (B) LOCATION: 4
        (D) OTHER INFORMATION: Lys-BOC (ix) FEATURE:
        (A) NAME/KEY: Modified-site
        (B) LOCATION: 5
        (D) OTHER INFORMATION: Lys-BOC (ix) FEATURE:
        (A) NAME/KEY: Modified-site
        (B) LOCATION: 6
        (D) OTHER INFORMATION: Lys-BOC (ix) FEATURE:
        (A) NAME/KEY: Modified-site
        (B) LOCATION: 7
        (D) OTHER INFORMATION: Lys-BOC (ix) FEATURE:
        (A) NAME/KEY: Modified-site
        (B) LOCATION: 8
        (D) OTHER INFORMATION: Lys-BOC (ix) FEATURE:
        (A) NAME/KEY: Modified-site
        (B) LOCATION: 9

```
            (D) OTHER INFORMATION: Gly-PAM (xi) SEQUENCE DESCRIPTION: SEQ ID NO:13:

Gly Gly Gly Lys Lys Lys Lys Lys Gly
1               5

(2) INFORMATION FOR SEQ ID NO:14:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (iii) HYPOTHETICAL: NO (ix) FEATURE:
        (A) NAME/KEY: Modified-site
        (B) LOCATION: 4
        (D) OTHER INFORMATION: Lys-BOC (ix) FEATURE:
        (A) NAME/KEY: Modified-site
        (B) LOCATION: 5
        (D) OTHER INFORMATION: Lys-BOC (ix) FEATURE:
        (A) NAME/KEY: Modified-site
        (B) LOCATION: 6
        (D) OTHER INFORMATION: Lys-BOC (ix) FEATURE:
        (A) NAME/KEY: Modified-site
        (B) LOCATION: 7
        (D) OTHER INFORMATION: Lys-BOC (ix) FEATURE:
        (A) NAME/KEY: Modified-site
        (B) LOCATION: 8
        (D) OTHER INFORMATION: Lys-BOC (ix) FEATURE:
        (A) NAME/KEY: Modified-site
        (B) LOCATION: 9
        (D) OTHER INFORMATION: Lys-BOC (ix) FEATURE:
        (A) NAME/KEY: Modified-site
        (B) LOCATION: 10
        (D) OTHER INFORMATION: Lys-BOC (ix) FEATURE:
        (A) NAME/KEY: Modified-site
        (B) LOCATION: 11
        (D) OTHER INFORMATION: Gly-PAM (xi) SEQUENCE DESCRIPTION: SEQ ID NO:14:

Gly Gly Gly Lys Lys Lys Lys Lys Lys Lys Gly
1               5                   10

(2) INFORMATION FOR SEQ ID NO:15:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (iii) HYPOTHETICAL: NO (ix) FEATURE:
        (A) NAME/KEY: Modified-site
        (B) LOCATION: 4
```

```
            (D) OTHER INFORMATION: Lys-BOC-Ser(benzyl)

(ix) FEATURE:
          (A) NAME/KEY: Modified-site
          (B) LOCATION: 5
          (D) OTHER INFORMATION: Lys-BOC-Ser(benzyl)

(ix) FEATURE:
          (A) NAME/KEY: Modified-site
          (B) LOCATION: 6
          (D) OTHER INFORMATION: Lys-BOC-Ser(benzyl)

(ix) FEATURE:
          (A) NAME/KEY: Modified-site
          (B) LOCATION: 7
          (D) OTHER INFORMATION: Lys-BOC-Ser(benzyl)

(ix) FEATURE:
          (A) NAME/KEY: Modified-site
          (B) LOCATION: 8
          (D) OTHER INFORMATION: Lys-BOC-Ser(benzyl)

(ix) FEATURE:
          (A) NAME/KEY: Modified-site
          (B) LOCATION: 9
          (D) OTHER INFORMATION: Gly-OCH2-PAM (xi) SEQUENCE DESCRIPTION: SEQ ID NO:15:

Gly Gly Gly Lys Lys Lys Lys Lys Gly
1               5
```